(12) United States Patent
Ebisawa et al.

(10) Patent No.: US 9,028,976 B2
(45) Date of Patent: May 12, 2015

(54) ORGANIC EL DEVICE

(75) Inventors: Akira Ebisawa, Toyko (JP); Hajime Amano, Toyko (JP); Sumiko Kitagawa, Toyko (JP); Tetsushi Inoue, Toyko (JP)

(73) Assignee: Futaba Corporation (JP)

( * ) Notice: Subject to any disclaimer, the term of this patent is extended or adjusted under 35 U.S.C. 154(b) by 380 days.

(21) Appl. No.: 13/118,273

(22) Filed: May 27, 2011

(65) Prior Publication Data
US 2011/0295017 A1 Dec. 1, 2011

(30) Foreign Application Priority Data
May 28, 2010 (JP) .................................. 2010-122772

(51) Int. Cl.
*H01L 51/50* (2006.01)
*C07C 13/70* (2006.01)
(Continued)

(52) U.S. Cl.
CPC .............. *C07D 209/86* (2013.01); *H01L 51/50* (2013.01); *H01L 51/5012* (2013.01);
(Continued)

(58) Field of Classification Search
CPC .. C07C 13/62; C07C 211/54; C07C 2103/52; C07C 2103/24; C07D 213/06; C07D 209/86; H01L 51/50; H01L 51/5012; C09K 11/00
See application file for complete search history.

(56) References Cited

U.S. PATENT DOCUMENTS 5,635,308 A 6/1997 Inoue et al.
7,097,917 B1 8/2006 Fujita et al.
(Continued)

FOREIGN PATENT DOCUMENTS

CN 101410356 4/2009
CN 101595080 12/2009
(Continued)

OTHER PUBLICATIONS

Notification of Reasons for Rejection, JP Application No. 2010-122772, dated Sep. 17, 2013, 4 pages.
(Continued)

Primary Examiner — Dawn Garrett
(74) Attorney, Agent, or Firm — Wong & Rees LLP; Kirk D. Wong

(57) ABSTRACT

A highly stable organic EL material having the properties of both benzofluoranthene and anthracene structures is provided. The organic EL device has at least one organic compound layer containing a compound presented by the general formula (I) below:

[Chem 1]

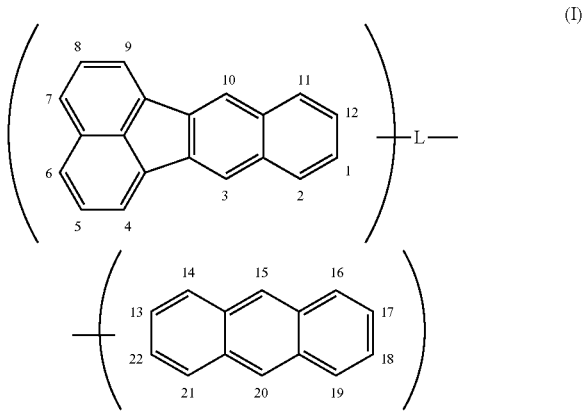

(in which L is a linking group linking any one of the positions 1 to 12 and any one of the positions 13 to 22; the unlinked positions 1 to 22 are substituted by any of a hydrogen atom, substituted or unsubstituted aryl group, substituted or unsubstituted heterocyclic group, substituted or unsubstituted alkyl group, and aromatic amino group; and L presents any of a single bond, substituted or unsubstituted arylene group, substituted or unsubstituted heterocyclic group, and substituted or unsubstituted alkylene group).

6 Claims, 1 Drawing Sheet

(51) Int. Cl.
  *C07C 211/54* (2006.01)
  *C07D 209/86* (2006.01)
  *C07D 211/04* (2006.01)
  *C09K 11/00* (2006.01)
  *C07C 13/62* (2006.01)
  *C07D 213/06* (2006.01)

(52) U.S. Cl.
  CPC ............... *C09K 11/00* (2013.01); *C07C 13/62* (2013.01); *C07C 211/54* (2013.01); *C07C 2103/24* (2013.01); *C07C 2103/52* (2013.01); *C07D 213/06* (2013.01); *Y10S 428/917* (2013.01)

(56) References Cited

U.S. PATENT DOCUMENTS

| | | | |
|---|---|---|---|
| 2004/0076853 A1* | 4/2004 | Jarikov | 428/690 |
| 2007/0243411 A1* | 10/2007 | Takashima et al. | 428/690 |
| 2009/0015144 A1* | 1/2009 | Takashima et al. | 313/504 |
| 2010/0176716 A1* | 7/2010 | Igawa et al. | 313/504 |

FOREIGN PATENT DOCUMENTS

| | | | |
|---|---|---|---|
| JP | 08-012600 | * | 1/1996 |
| JP | H08-012600 | | 1/1996 |
| JP | 2001-213814 | * | 8/2001 |
| JP | 2001-257075 | * | 9/2001 |
| JP | 2001-267078 | * | 9/2001 |
| JP | 2003-026616 | * | 1/2003 |
| JP | 2001-267078 | | 9/2007 |
| JP | 2009-001499 | * | 1/2009 |
| JP | 2011-176204 | | 9/2011 |
| WO | WO 2007/100010 | | 9/2007 |

OTHER PUBLICATIONS

The State Intellectual Property Office of the People's Republic of China "Notification of First Office Action" received in CN patent application No. 201110141564.3, dated May 24, 2013, 11 pages.

* cited by examiner

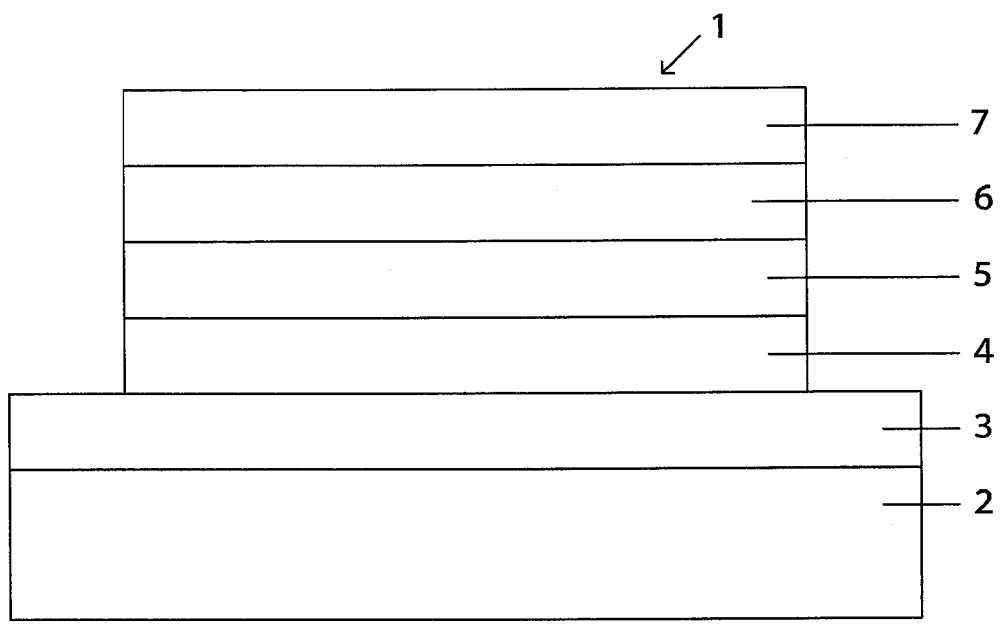

ORGANIC EL DEVICE

CROSS-REFERENCE TO RELATED APPLICATION

This U.S. Non-Provisional Patent Application claims the benefit of Japanese Patent Application No. 2010-122772, filed on May 28, 2010, the entire disclosure of which is incorporated by reference herein.

FIELD

This application relates to an organic EL (electro-luminescence) device.

BACKGROUND

Organic EL devices are able to emit light with a voltage as low as several V to several tens V. Furthermore, organic EL devices are able to emit different color lights by selecting the class of fluorescent organic compounds. Therefore, application of organic EL devices to various light emitting devices and display devices are expected. For example, Unexamined Japanese Patent Application KOKAI Publication Nos. 2001-257075, 2003-26616 and H08-12600 have proposed materials having various structures including fluoranthene and anthracene structures as the host material or light emitting material of blue light emitting devices.

The fluoranthene structure, particularly benzofluoranthene structure yields a significantly high fluorescence intensity and has an energy gap suitable for the host material or light emitting material of blue light emitting devices. Therefore, the fluoranthene structure has always been treated as a blue light emitting material candidate; however, it has not achieved properties suitable for practical use.

On the other hand, the anthracene structure is a significantly potent structure as a highly efficient and long life organic EL host material. Particularly, the anthracene structure plays a key role as the host material of blue light emitting devices. However, since blue light emitting devices having a much longer life is demanded and slight change in physical properties is required for dealing with more complex device structures, the anthracene structure is not always a satisfactory blue light emitting material.

Cross-coupling of materials of different structures is considered to be a means for developing a new material for dealing with such slight change in physical properties. Combing two different structures, cross-coupling allows their respective properties to realize in one material, covering a wider range of device structures. A combination of benzofluoranthene and anthracene structures can be a potent combination as a blue light emitting material.

SUMMARY

The present invention is invented in view of the above circumstances and an exemplary object of the present invention is to provide an organic EL material having the properties of both benzofluoranthene and anthracene structures.

In order to achieve the above object, the organic EL device of the present invention has at least one organic compound layer containing a compound presented by the general formula (I) below:

[Chem 1]

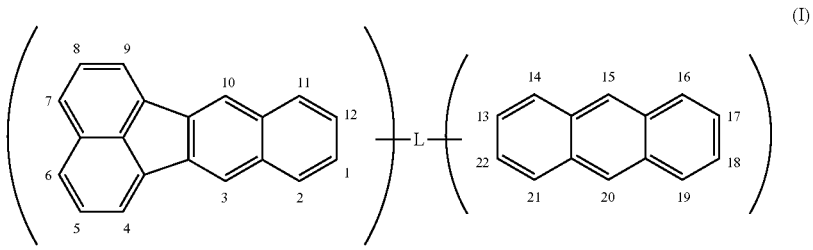

(I)

(in which L is a linking group linking any one of the positions 1 to 12 and any one of the positions 13 to 22; the unlinked positions 1 to 22 are substituted by any of a hydrogen atom, substituted or unsubstituted aryl group, substituted or unsubstituted heterocyclic group, substituted or unsubstituted alkyl group, and aromatic amino group; and L presents any of a single bond, substituted or unsubstituted arylene group, substituted or unsubstituted heterocyclic group, and substituted or unsubstituted alkylene group).

Preferably, the L links any one of the positions 1 to 5 and 8 to 12 and any one of the positions 13 to 22.

Preferably, the L links any one of the positions 1, 2, 4, 5, 8, 9, 11, and 12 and any one of the positions 13 to 22.

Preferably, the L links the position 1 or 12 and any one of the positions 13 to 22.

Preferably, the compound is presented by the general formula (II) or general formula (III) below:

[Chem 2]

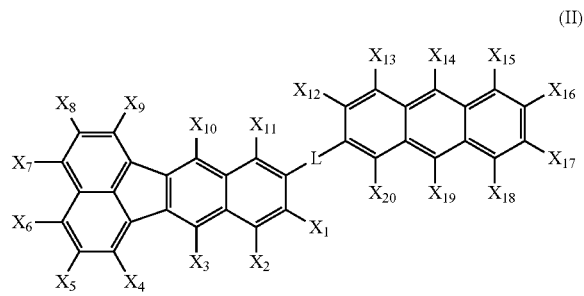

(II)

[Chem 3]

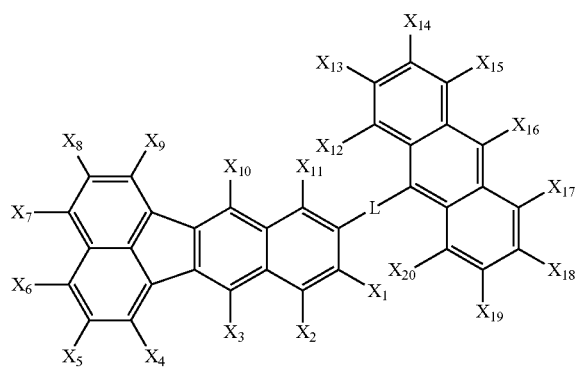

(III)

BRIEF DESCRIPTION OF THE DRAWINGS

A more complete understanding of this application can be obtained when the following detailed description is considered in conjunction with the following drawings, in which:

FIG. 1 is an illustration showing an exemplary structure of the organic EL device of the present invention.

DETAILED DESCRIPTION

A specific structure of the organic EL device of the present invention will be described hereafter. The organic EL device of the present invention has at least one organic compound layer containing a compound presented by the general formula (I) below:

[Chem 4]

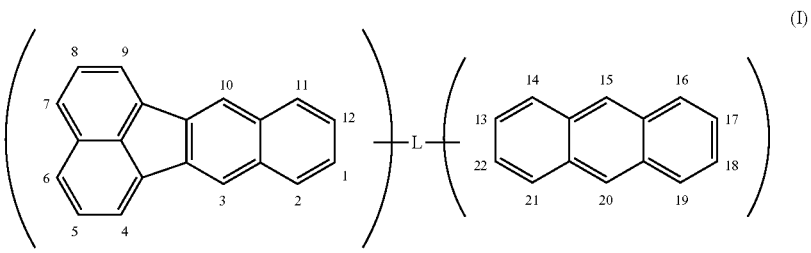

(I)

(in which $X_1$ to $X_{20}$ present any of a hydrogen atom, substituted or unsubstituted aryl group, substituted or unsubstituted heterocyclic group, substituted or unsubstituted alkyl group, and aromatic amino group; and L is a linking group and presents any of a single bond, substituted or unsubstituted arylene group, substituted or unsubstituted heterocyclic group, and substituted or unsubstituted alkylene group).

Preferably, $X_3$, $X_6$, $X_7$, $X_{10}$, $X_{14}$, $X_{16}$, and $X_{19}$ in the general formula (II) are substituted.

Preferably, $X_3$, $X_{10}$, $X_{14}$, and $X_{19}$ in the general formula (II) are substituted.

Preferably, $X_3$, $X_6$, $X_7$, $X_{10}$, $X_{13}$, $X_{16}$, and $X_{18}$ in the general formula (III) are substituted.

Preferably, $X_3$, $X_{10}$, and $X_{16}$ in the general formula (III) are substituted.

The linking group L is, for example, a single bond or a substituted or unsubstituted arylene group.

The organic compound layer is, for example, a light emitting layer.

The organic compound layer is, for example, a carrier transport layer.

(in which L is a linking group linking any one of the positions 1 to 12 and any one of the positions 13 to 22 provided that the numbers in the formula present the positions linked by the linking group L; the unlinked positions 1 to 22 are substituted by any of a hydrogen atom, substituted or unsubstituted aryl group, substituted or unsubstituted heterocyclic group, substituted or unsubstituted alkyl group, and aromatic amino group; and L presents any of a single bond, substituted or unsubstituted arylene group, substituted or unsubstituted heterocyclic group, and substituted or unsubstituted alkylene group).

For example, use of the above compound in the light emitting layer allows for efficient light emission of a doping material that does not work because of the energy levels when a prior art host mistrial is used. Furthermore, use of the above compound in the carrier transport layer allows for control of the electron or hole transport rate, which cannot be adjusted with a prior art transport material.

The aryl group in the general formula (I) can be monocyclic or polycyclic and includes condensed rings and clusters of rings. Such an aryl group preferably has a total of 6 to 20 carbon atoms. Examples of the aryl group include phenyl, (o-, m-, p-) tolyl, phenanthryl, pyrenyl, perylenyl, coronenyl, naphthyl, anthryl, (o-, m-, p-) biphenyl, phenylanthryl, and tolylanthryl groups. Particularly, a phenyl group is preferable. These aryl groups may further be substituted. Examples of such a substituent include alkyl, alkoxy, aryl, aryloxy, and amino groups and a halogen atom.

Examples of the heterocyclic group in the general formula (I) include five- or six-member aromatic heterocyclic groups containing O, N, and/or S as a hetero atom(s), and condensed polycyclic aromatic heterocyclic groups having 2 to 20 carbon atoms. Examples of the aromatic heterocyclic groups and condensed polycyclic aromatic heterocyclic groups include thienyl, furyl, pyrrolyl, pyridyl, quinolyl, and quinoxalyl groups. These heterocyclic groups may further be substituted. Examples of such a substituent include alkyl, alkoxy, aryl, aryloxy, and amino groups and a halogen atom.

The alkyl group in the general formula (I) can be liner or branched. Such an alkyl group preferably has 1 to 10 carbon atoms. Examples of the alkyl group include methyl, ethyl, (n-, i-) propyl, and (n-, i-, s-, t-) butyl groups. These alkyl groups may have a substituent. Examples of such a substituent include alkyl, alkoxy, aryl, aryloxy, and amino groups and a halogen atom.

The aromatic amino group in the general formula (I) can be unsubstituted or substituted; preferably, it is substituted. Examples of the aromatic amino group include diphenylamino, ditolylamino, dibiphenylamino, N-phenyl-N-tolylamino, N-phenyl-N-naphthyl amino, N-phenyl-N-biphenylamino, N-phenyl-N-anthrylamino, N-phenyl-N-pyrenylamino, dinaphthylamino, dianthrylamino, and dipyrenylamino groups.

Examples of the arylene group of the linking group L include ordinary arylene groups such as phenylene, biphenylene, and anthrylene groups, and two or more directly-connected arylene groups. Furthermore, the arylene group of the linking group L may consist of two or more arylene groups connected via an alkylene group, —O—, —S—, or —NR— in which R is an alkyl or aryl group. The aryl group may further be substituted. Examples of such a substituent include alkyl, alkoxy, aryl, aryloxy, and amino groups and a halogen atom.

Examples of the heterocyclic group of the linking group L include five- or six-member aromatic heterocyclic groups containing O, N, and/or S as a hetero atom(s), and condensed polycyclic aromatic heterocyclic groups having 2 to 20 carbon atoms. Examples of the aromatic heterocyclic groups and condensed polycyclic aromatic heterocyclic groups include thienyl, furyl, pyrrolyl, pyridyl, quinolyl, and quinoxalyl groups. These heterocyclic groups may further be substituted. Examples of such a substituent include alkyl, alkoxy, aryl, aryloxy, and amino groups and a halogen atom.

The alkylene group of the linking group L is preferably a methylene or ethylene group.

Examples of the linking group L are given below; however, the present invention is not restricted to them.

[Chem 5]

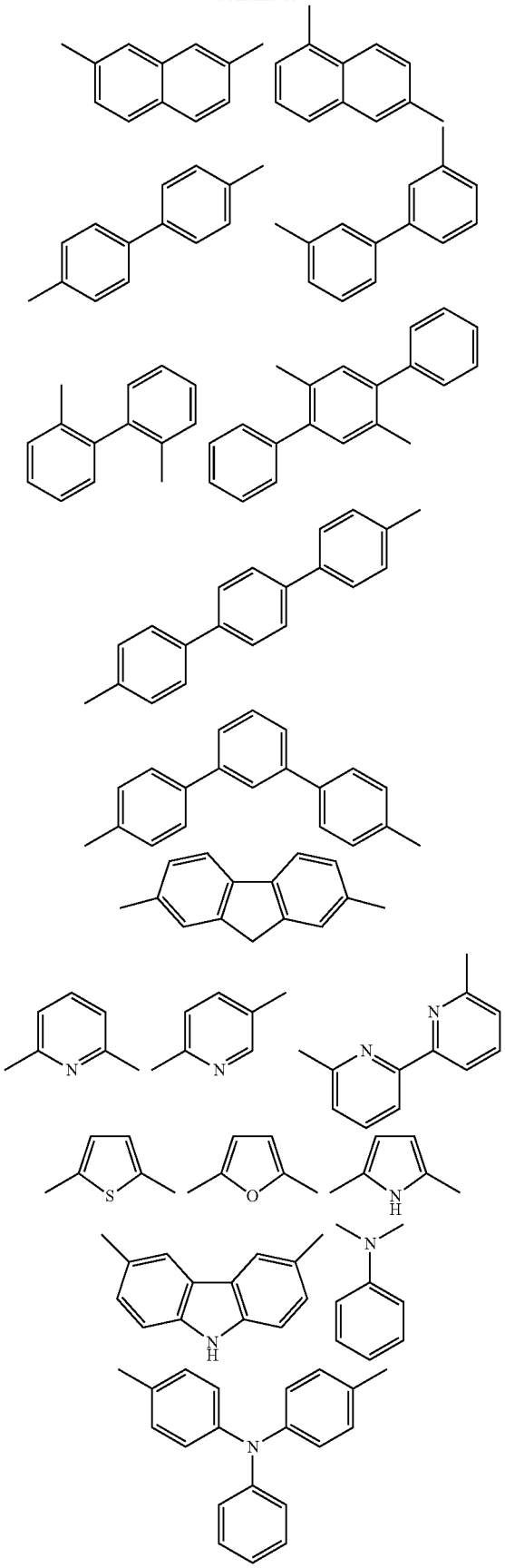

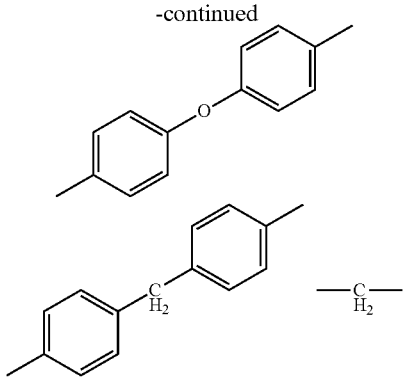

Preferably, the linking group L is a single bond or a substituted or unsubstituted arylene group. Furthermore, the substituted or unsubstituted arylene group is preferably a substituted or unsubstituted phenylene group.

The compound of the present invention preferably has a molecular weight of 1000 or lower. Preferably, the substituent is a substituted or unsubstituted aryl group and particularly a phenyl group. The other Xn is preferably a hydrogen atom.

In the compound of the present invention, preferably, the linking group L links any one of the positions 1 to 5 and 8 to 12 and any one of the positions 13 to 22. The linking at these positions makes difficult cyclization with the linking part structure under high temperatures such as during deposition and eliminates the risk of contaminants having long wavelength components being produced. Consequently, the occurrence of adverse effects such as shortened life and significant change in emitted light color is reduced.

In the compound of the present invention, more preferably, the linking group L links any one of the positions 1, 2, 4, 5, 8, 9, 11, and 12 and any one of the positions 13 to 22. The linking at these positions more likely reduces the occurrence of adverse effects such as shortened life and significant change in emitted light color.

In the compound of the present invention, most preferably, the linking group L links the position 1 or 12 and any of the positions 13 to 22. The linking at these positions most likely reduces the occurrence of adverse effects such as shortened life and significant change in emitted light color.

Particularly, it is preferable that the compound of the present invention is presented by the general formula (II) or general formula (III) below.

[Chem 6]

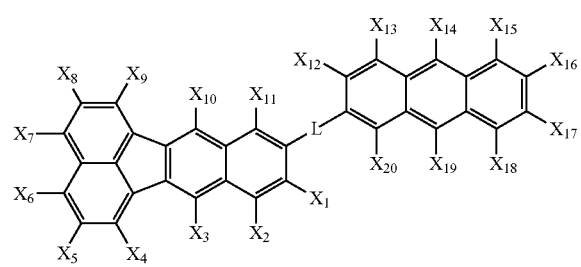

(II)

[Chem 7]

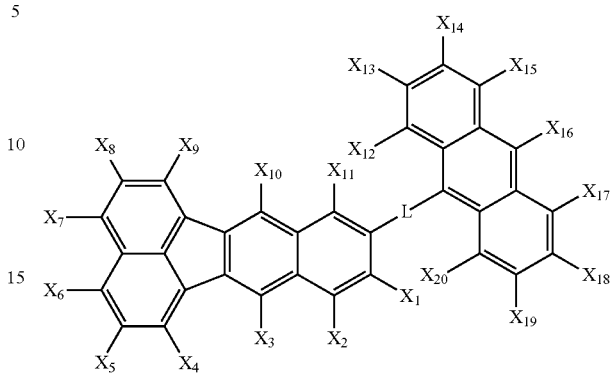

(III)

(in which $X_1$ to $X_{20}$ present any of a hydrogen atom, substituted or unsubstituted aryl group, substituted or unsubstituted heterocyclic group, substituted or unsubstituted alkyl group, and aromatic amino group; and L is a linking group and presents any of a single bond, substituted or unsubstituted arylene group, substituted or unsubstituted heterocyclic group, and substituted or unsubstituted alkylene group).

The aryl, heterocyclic, alkyl, aromatic amino, arylene, and alkylene groups in the general formulae (II) and (III) are the same as the aryl, heterocyclic, alkyl, aromatic amino, arylene, and alkylene groups in the general formula (I).

Preferably, $X_3$, $X_6$, $X_7$, $X_{10}$, $X_{14}$, $X_{16}$, and $X_{19}$ in the general formula (II) are substituted. Substituted at these positions, the material of the general formula (II) does not easily undergo crystallization and forms an excellent amorphous film. Furthermore, these are chemically highly active positions. If these substitution positions are free, they may be attacked by some active species during the operation of the device and cause some deterioration. Particularly, it is preferable that $X_3$, $X_{10}$, $X_{14}$, and $X_{19}$ in the general formula (II) are substituted. If these substitution positions are free, the fluorescence intensity may significantly be reduced.

Preferably, $X_3$, $X_6$, $X_7$, $X_{10}$, $X_{13}$, $X_{16}$, and $X_{18}$ in the general formula (III) are substituted. Substituted at these positions, the material of the general formula (III) does not easily undergo crystallization and forms an excellent amorphous film. Furthermore, these are chemically highly active positions. If these substitution positions are free, they may be attacked by some active species during the operation of the device and cause some deterioration. Particularly, it is preferable that $X_3$, $X_{10}$, and $X_{16}$ in the general formula (III) are substituted. If these substitution positions are free, the fluorescence intensity may significantly be reduced.

Examples of the compound of the present invention will be given below; however, the present invention is not restricted to them.

[Chem 8]
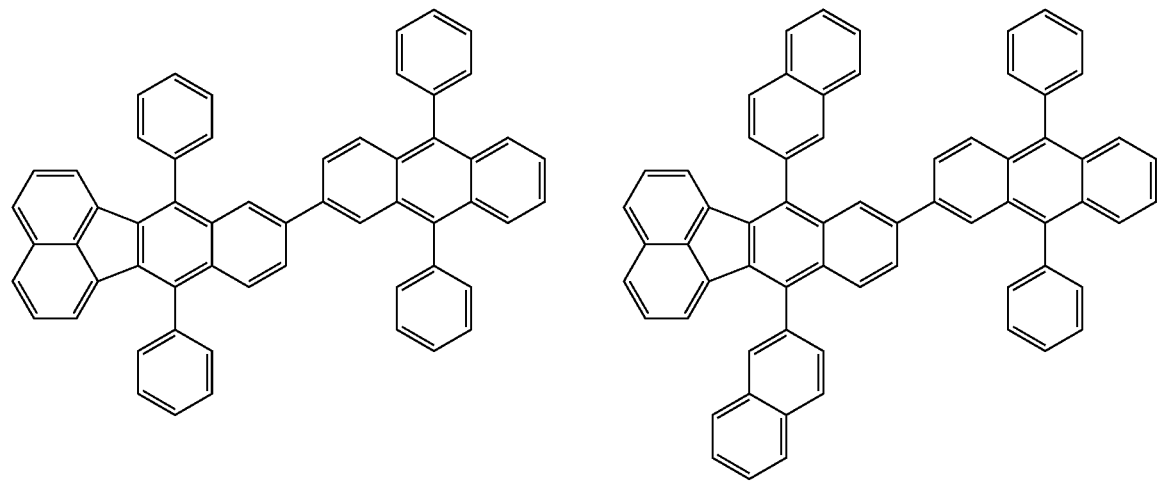
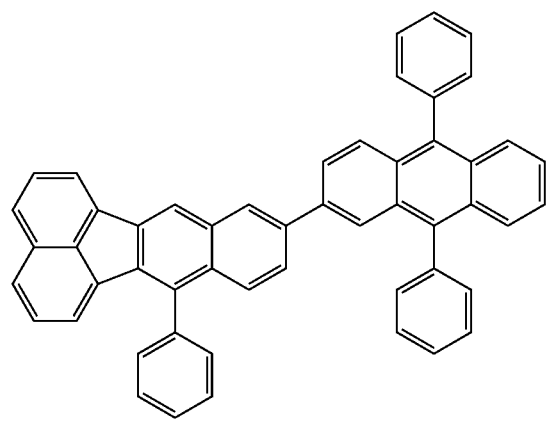
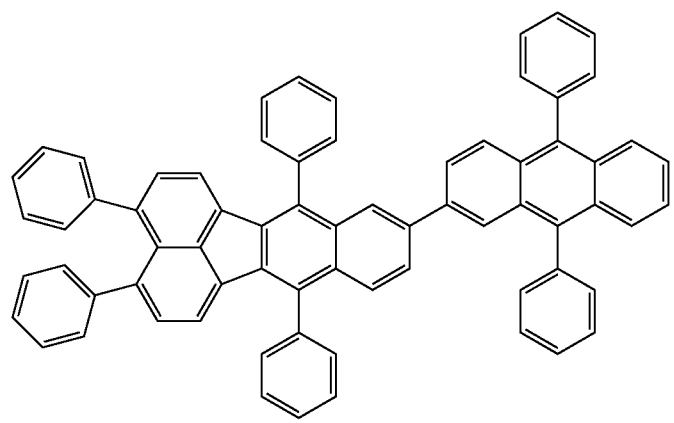

-continued
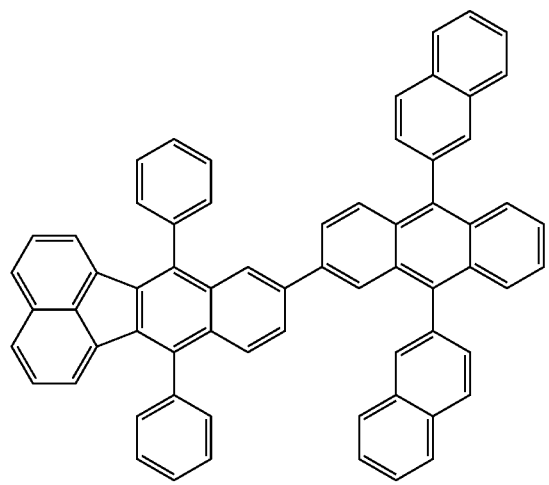
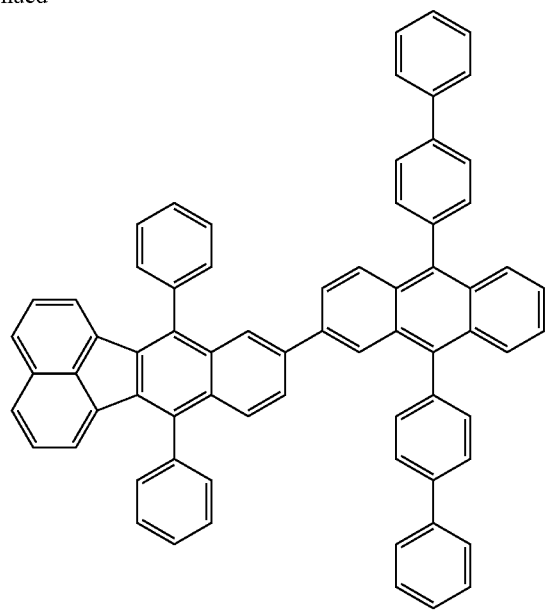
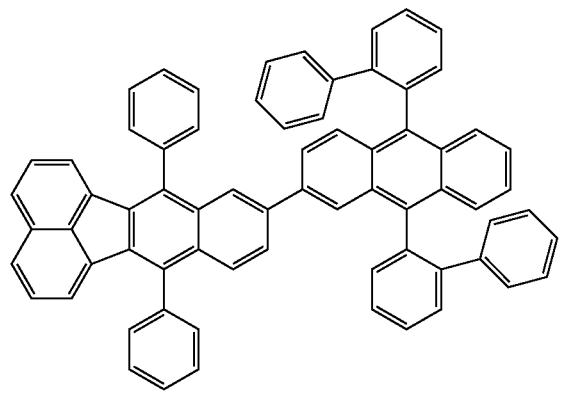
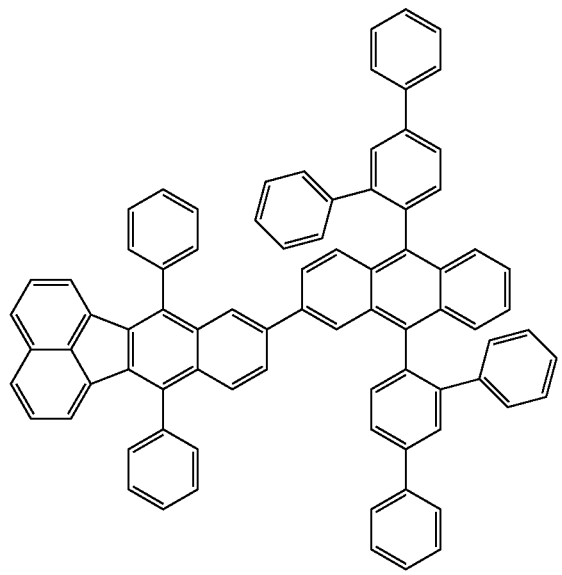
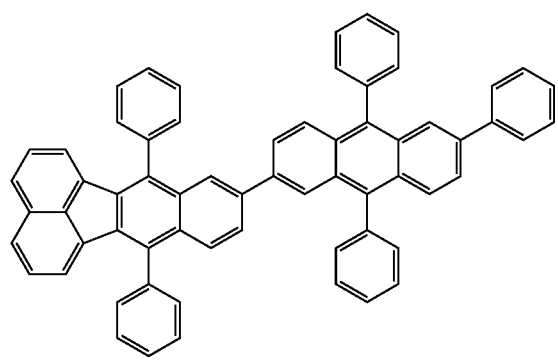
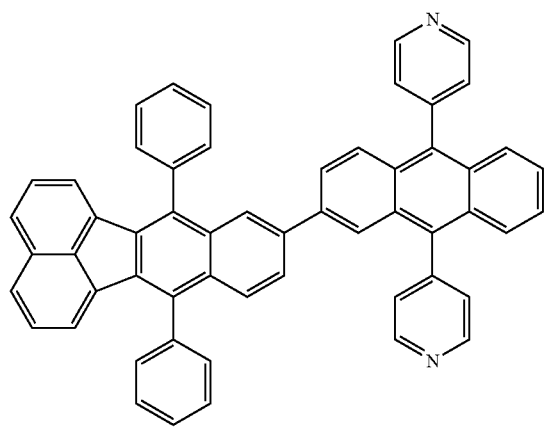

-continued
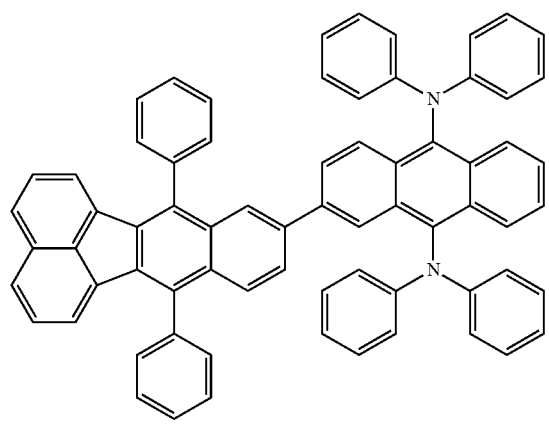
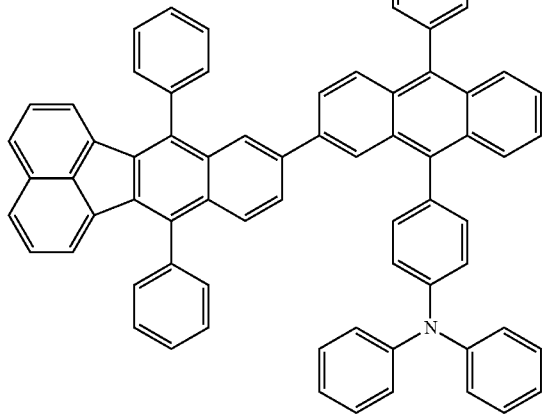
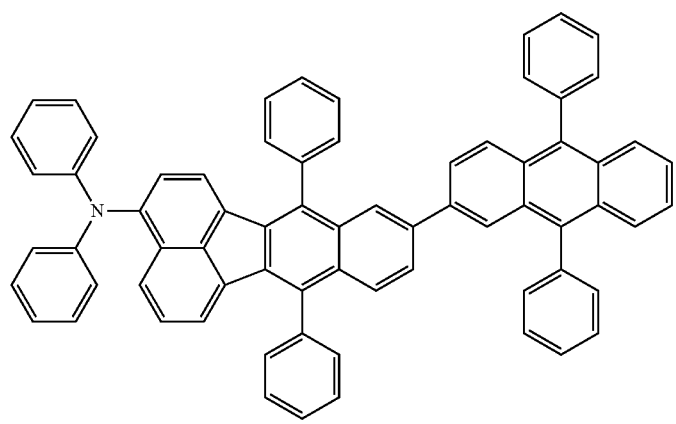
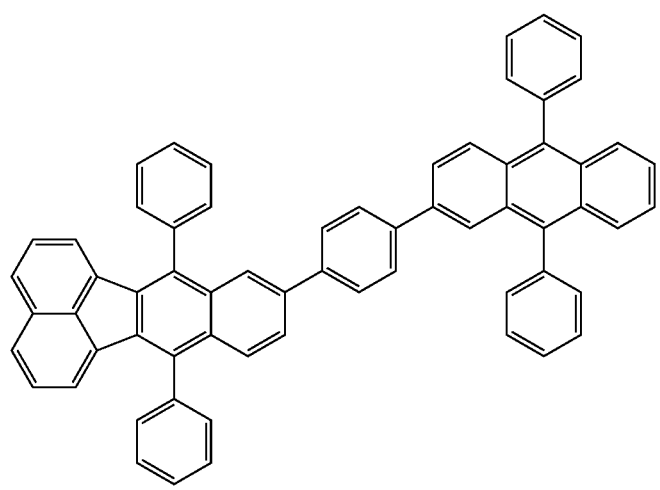

-continued
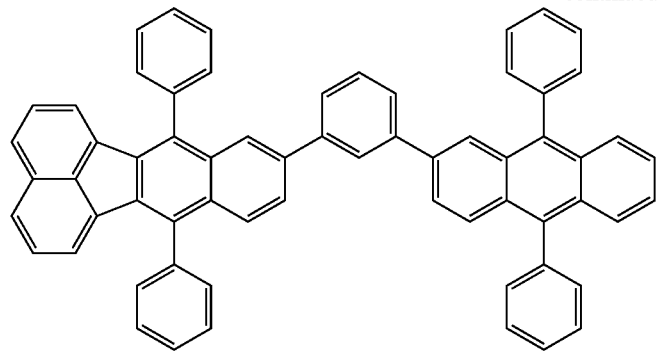
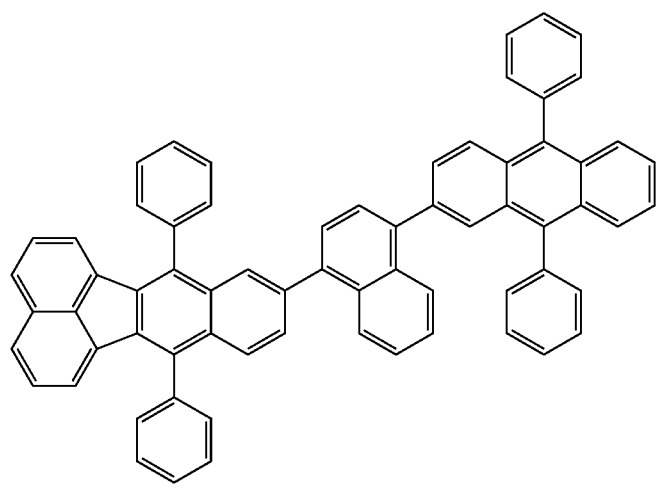
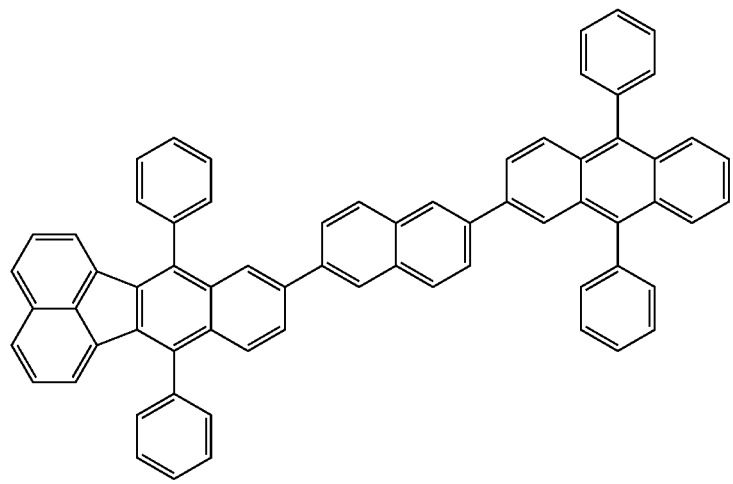
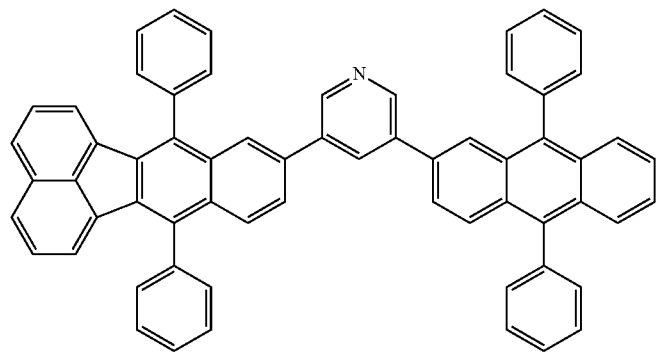

[Chem 9]
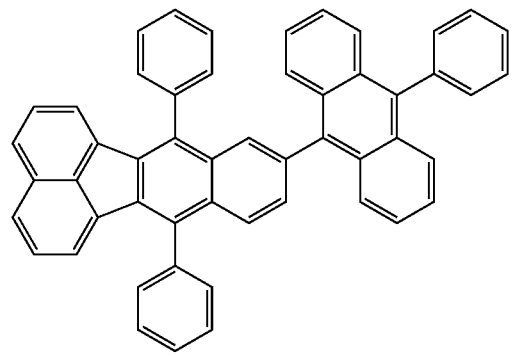

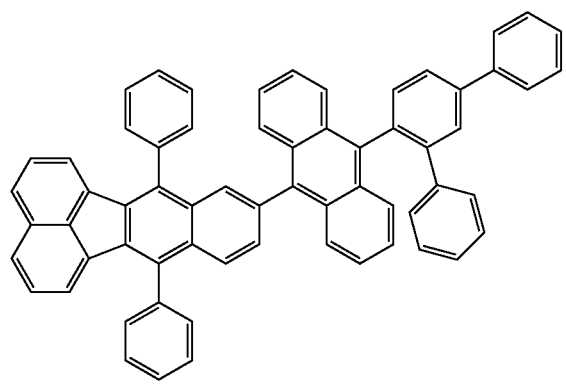
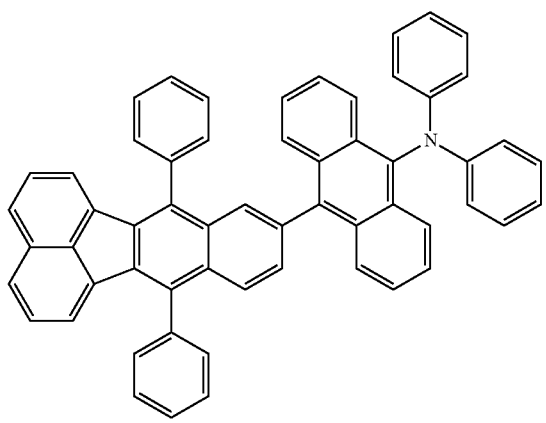
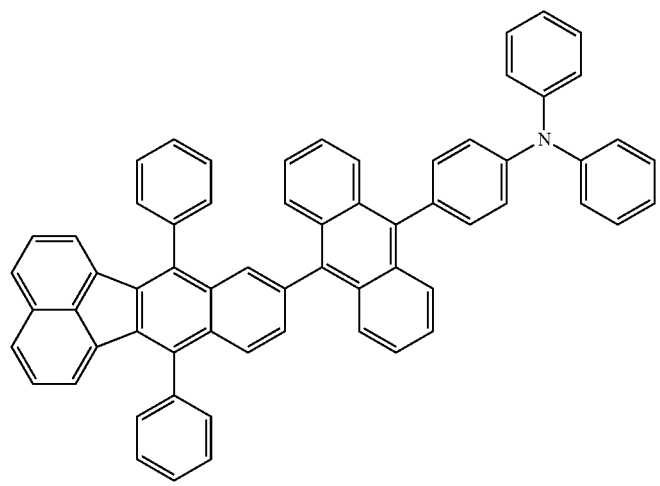
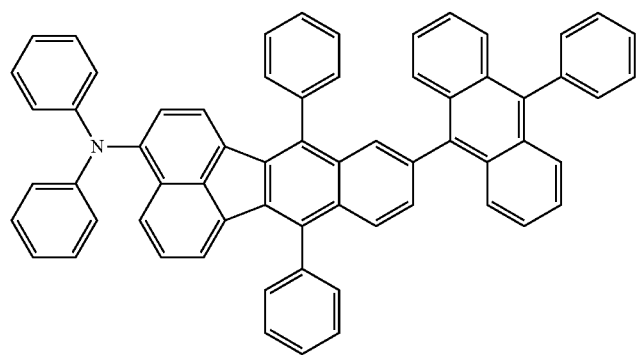
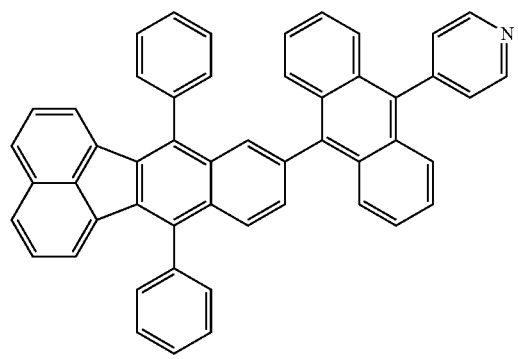
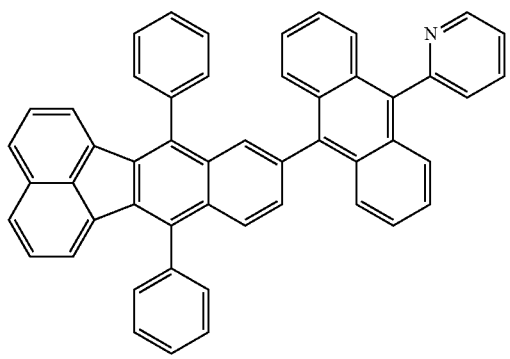

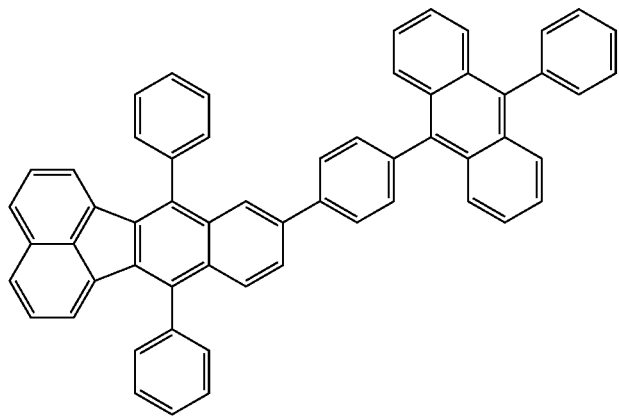
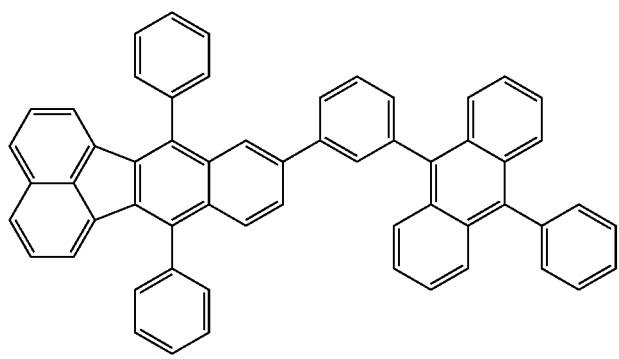
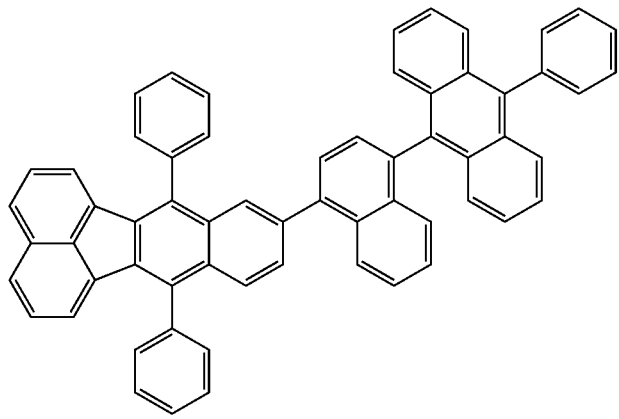
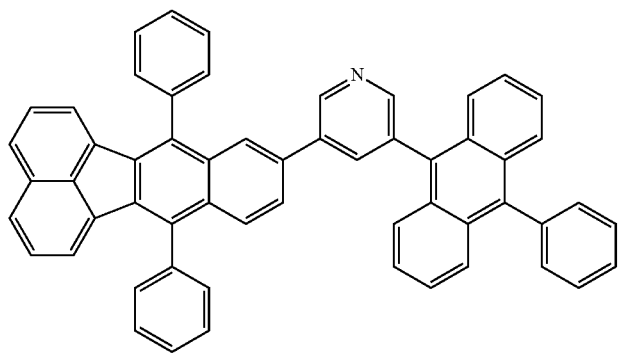

-continued
[Chem 10]
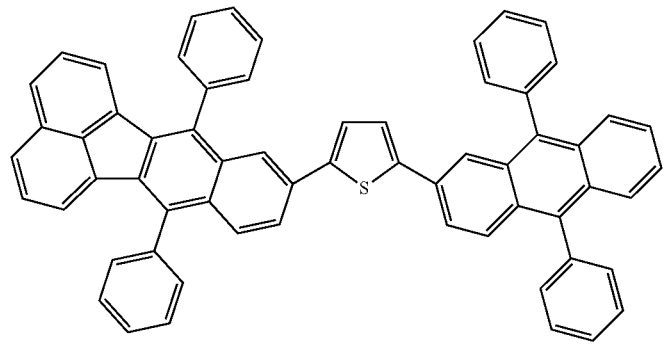
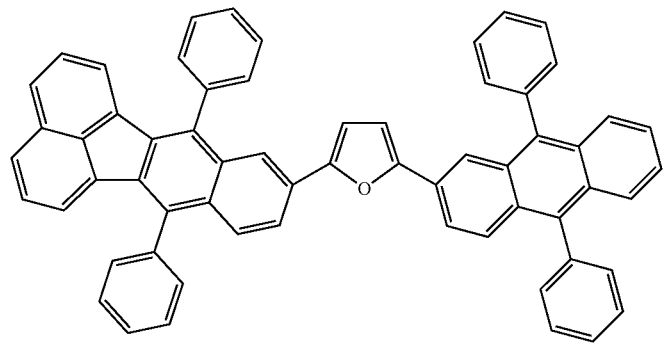
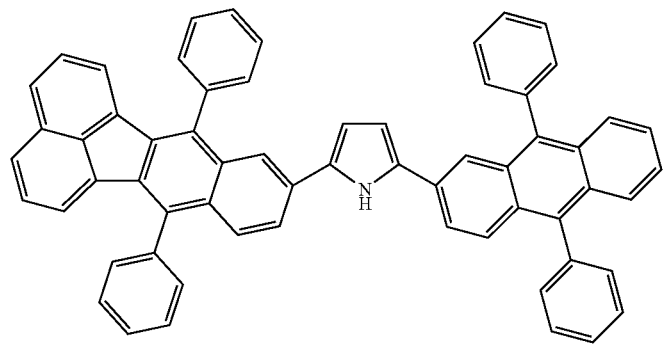
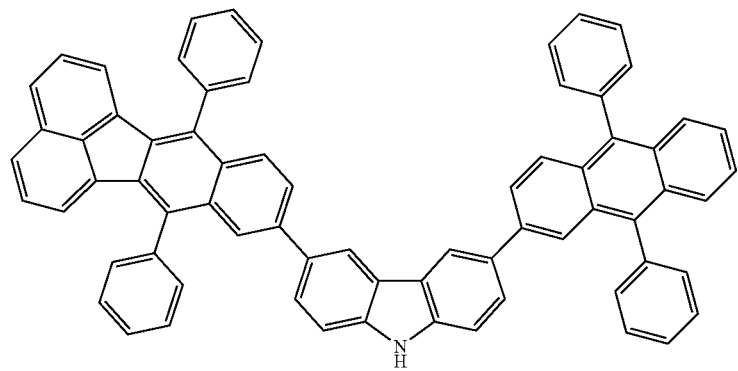

-continued
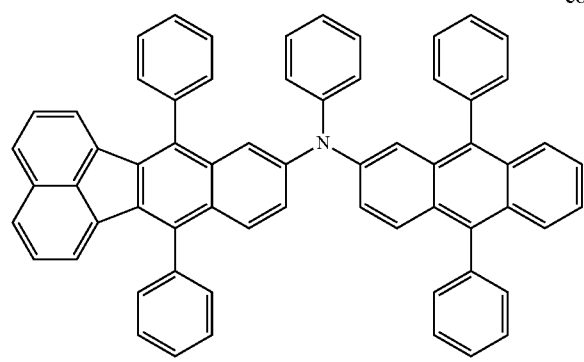
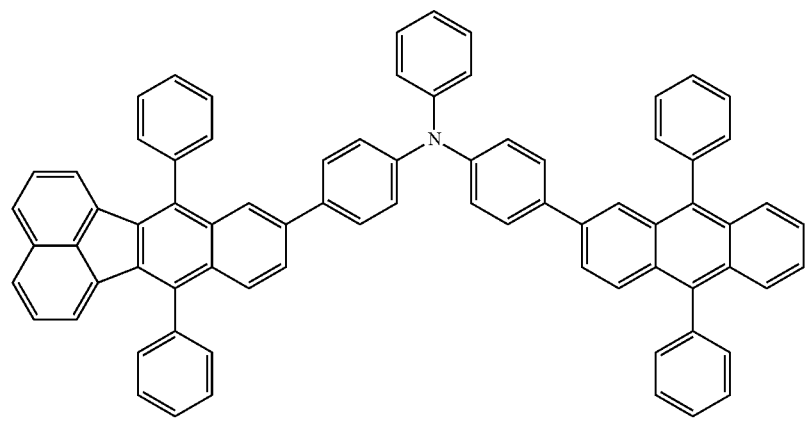
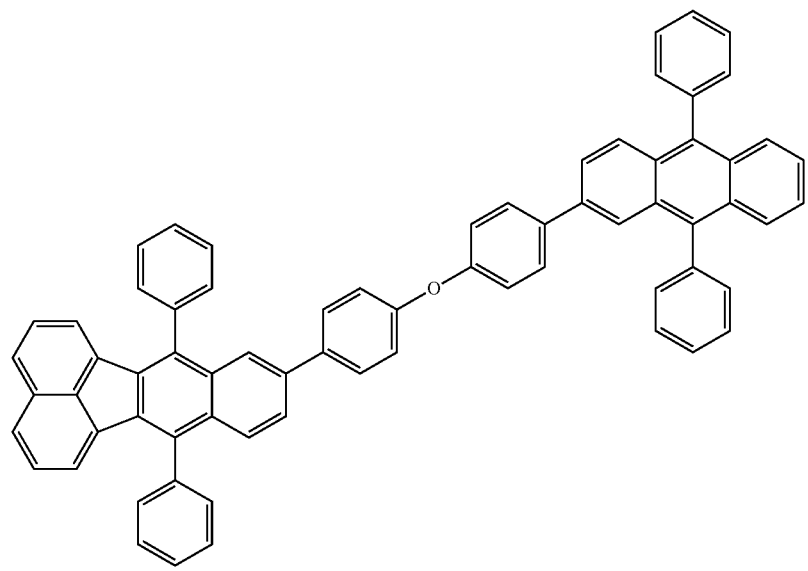

-continued
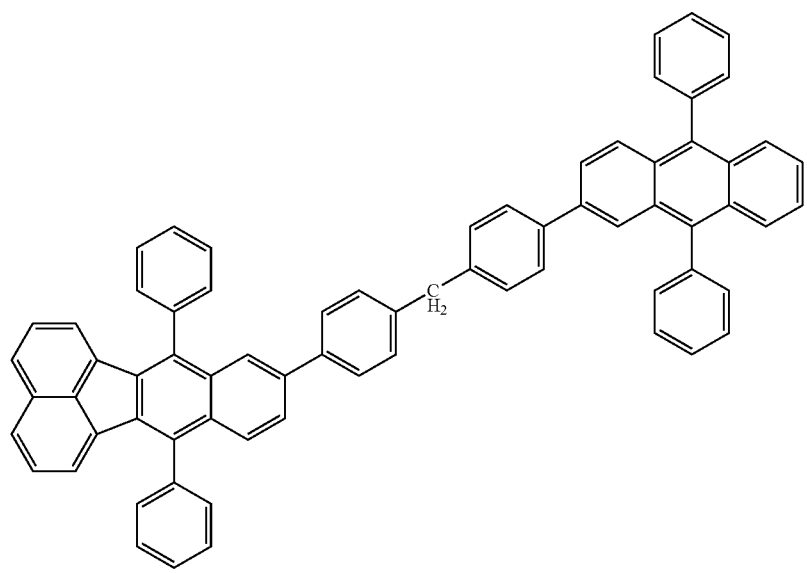
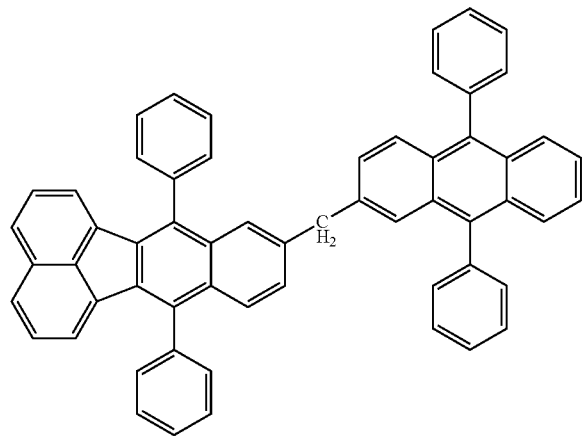
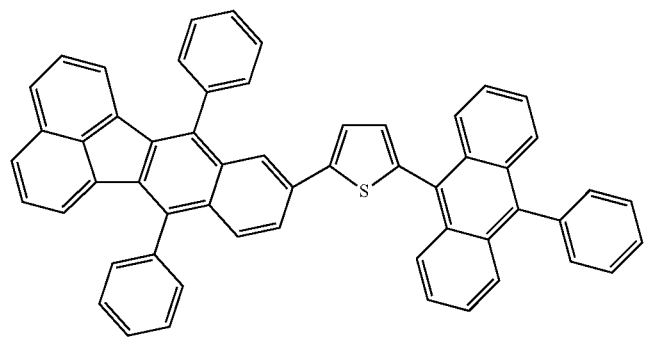
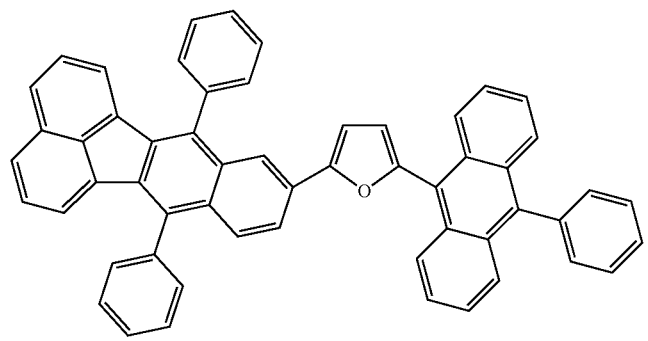

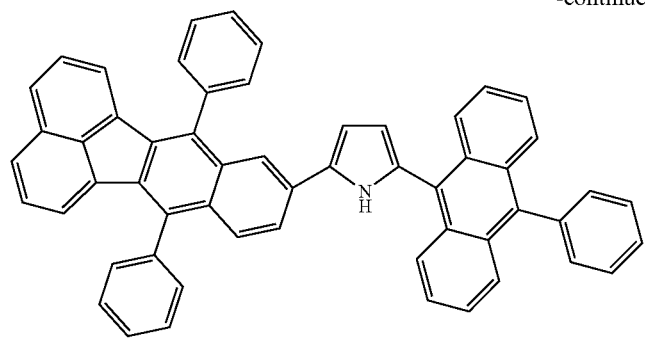
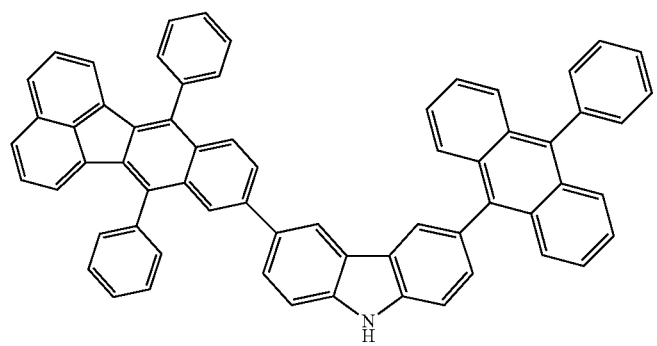
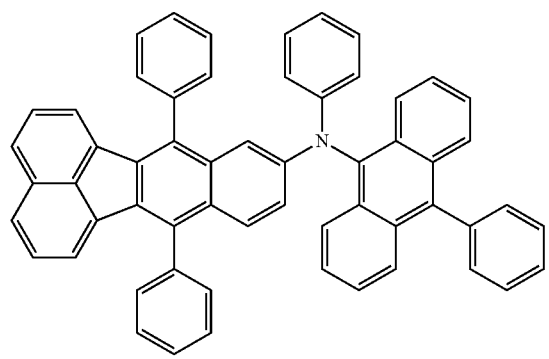
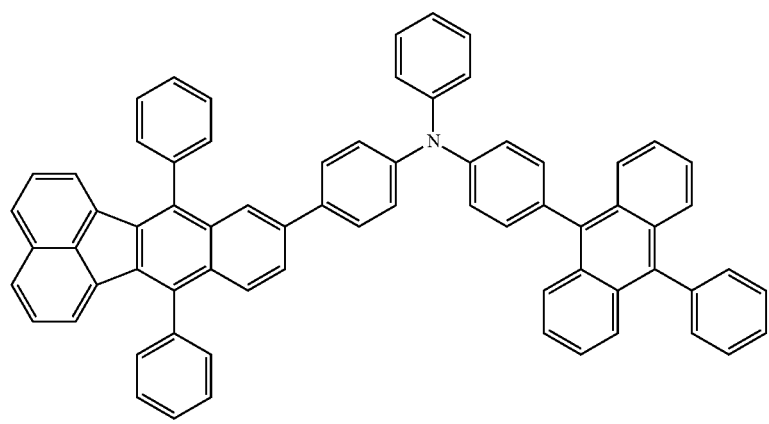

-continued
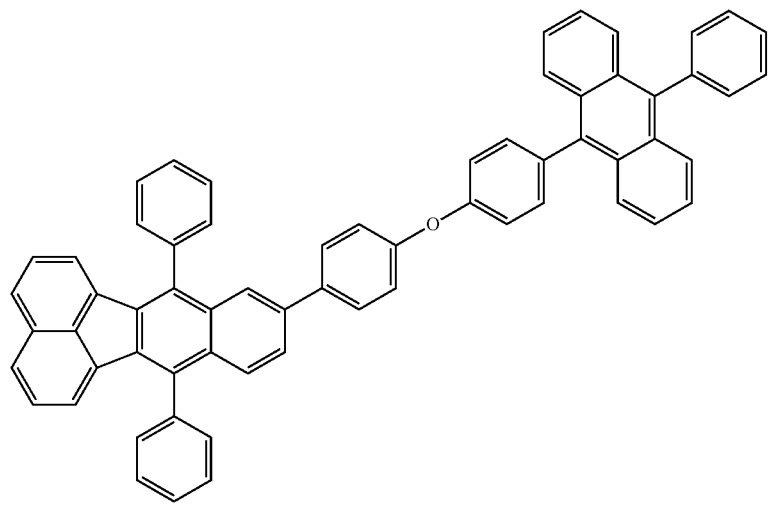
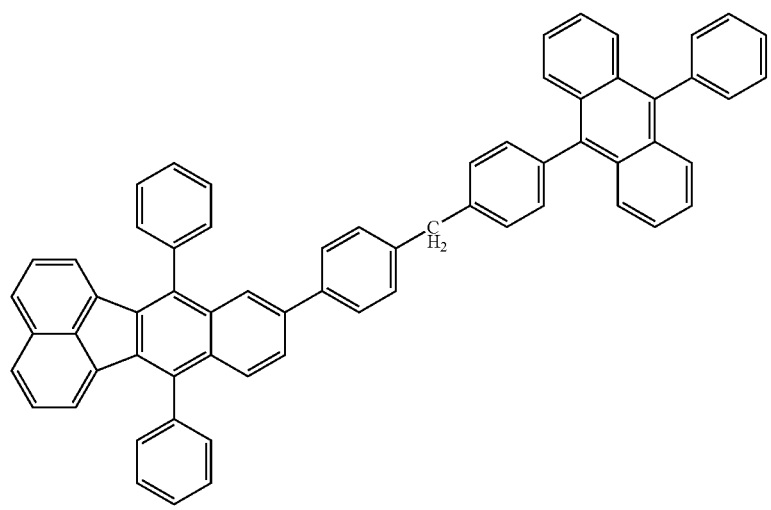
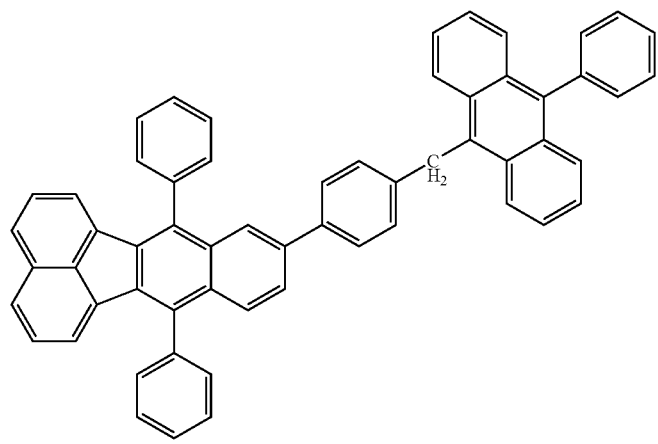

[Chem 11]
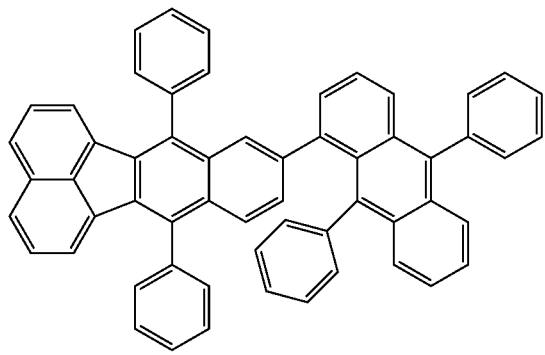
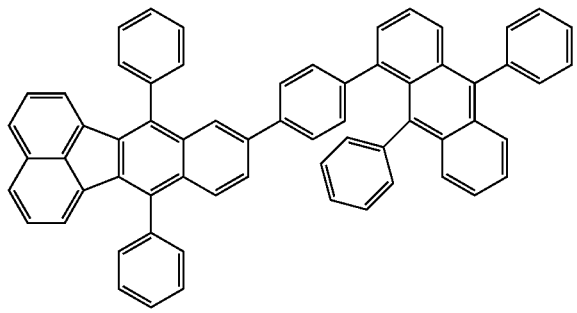
-continued
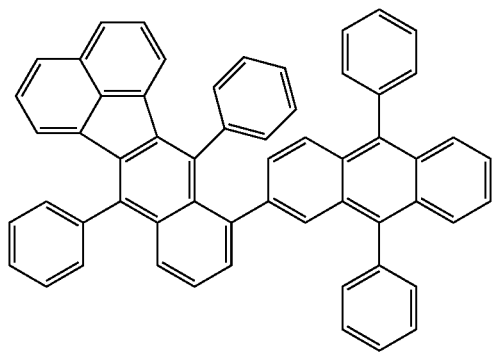
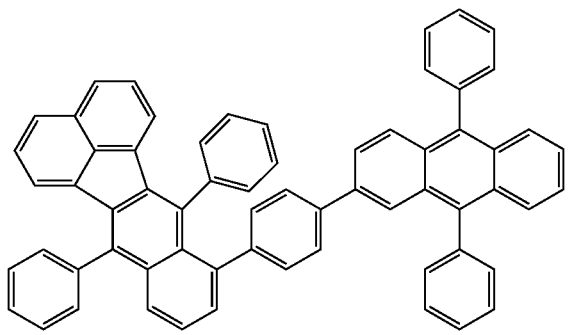
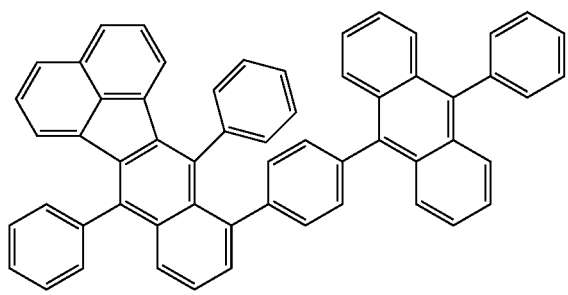
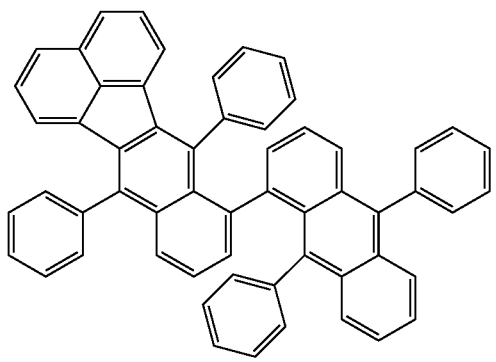
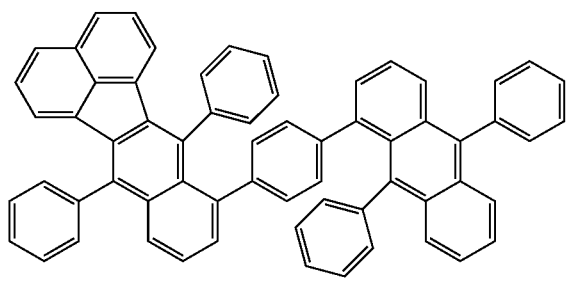
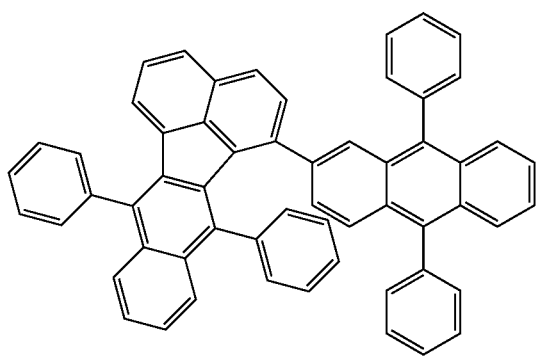

-continued
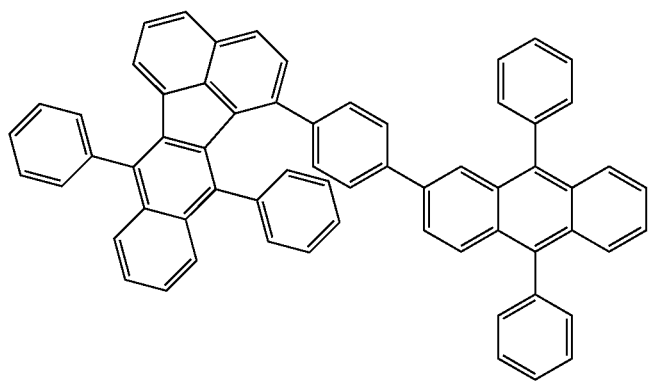
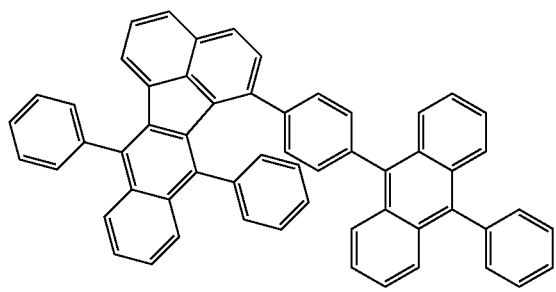
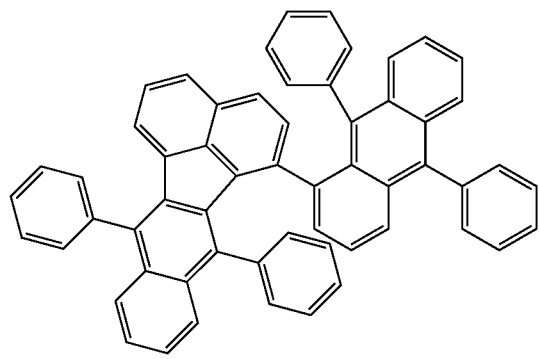
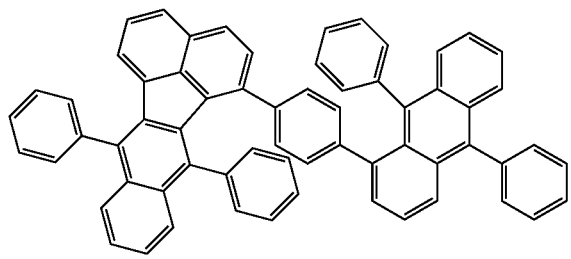
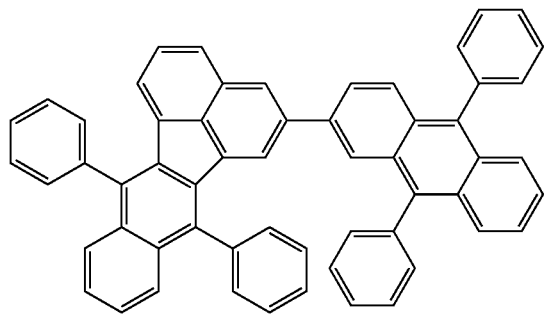
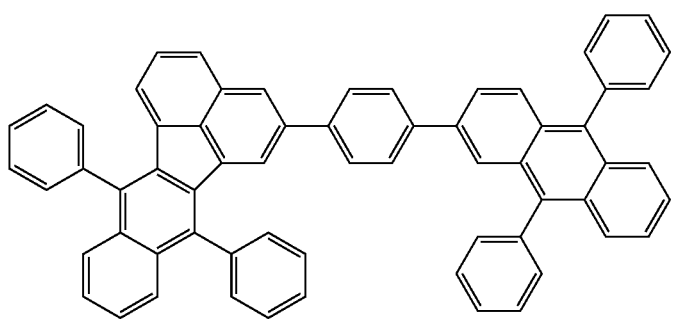
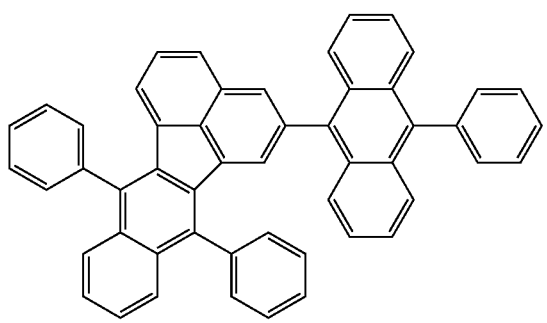

-continued

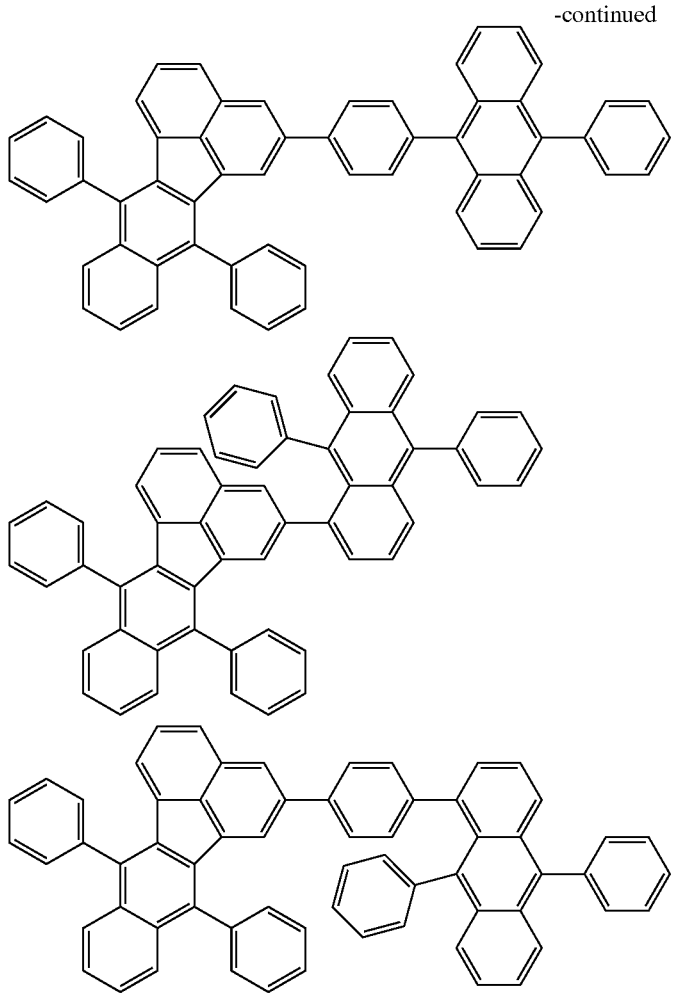

The organic EL device of the present invention having at least one organic compound layer containing the above compound will be described hereafter. FIG. 1 is an illustration showing an exemplary structure of the organic EL device of the present invention. As shown in FIG. 1, an organic EL device 1 of the present invention has, on a substrate 2, a positive electrode 3, a hole injection/transport layer 4, a light emitting layer 5, an electron injection/transport layer 6, and a negative electrode 7 in sequence.

The substrate 2 is preferably formed by a transparent or translucent material. The substrate 2 is formed by, for example, a glass plate, transparent plastic sheet, translucent plastic sheet, quartz, transparent ceramic, or a complex sheet consisting of a combination of them. However, the substrate 2 can be formed by an opaque material. In such a case, the organic EL device 1 has the layers arranged in the opposite order to those in FIG. 1. The substrate 2 may further be combined with, for example, a color filter film, color conversion film, and/or dielectric reflecting film to control the emitted light color.

The positive electrode 3 is preferably made of an electrode material such as a metal, alloy, and electricity-conducting compound having a relatively high work function. Examples of the electrode material of the positive electrode 3 include gold, platinum, silver, copper, cobalt, nickel, palladium, vanadium, tungsten, tin oxide, zinc oxide, ITO (indium tin oxide), polythiophene, and polypyrrole. These electrode materials may be used alone or in combination. The positive electrode 3 can be formed on the substrate 2 by the above electrode material through a vapor-phase growth process such as deposition and sputtering. Furthermore, the positive electrode 3 can have a monolayer or multilayer structure.

The hole injection/transport layer 4 contains a compound capable of facilitating injection of holes from the positive electrode 3, transporting the injected holes, and blocking electrons. The hole injection/transport layer 4 can be formed by using at least one of the following: phthalocyanine derivatives, triarylmethane derivatives, triarylamine derivatives, oxazole derivatives, hydrazone derivatives, stilbene derivatives, pyrazoline derivatives, polysilane derivatives, polyphenylvinylene and their derivatives, polythiophene and their derivatives, and poly-N-vinylcarbazole derivatives. Furthermore, the above compound of the present invention can be used in the hole injection/transport layer 4. In such a case, the hole transport rate can be controlled, which cannot be adjusted with any prior art hole injection/transport material. The compound capable of injecting/transporting holes can be used alone or in combination.

The light emitting layer 5 contains a compound capable of injecting holes and electrons, transporting them, and recoupling holes and electrons to generate excitons. It is preferable that the above compound is used in the light emitting layer 5 and the organic compound layer containing the above compound is the light emitting layer 5. Use of the above compound in the light emitting layer 5 allows for efficient light emission of a doping material that does not work due to the energy levels when a prior art host material is used.

The light emitting layer 5 of the present invention can contain other fluorescent materials in addition to the above compound. Examples of such fluorescent materials include quinacridone, rubrene, compounds such as styryl dyes, quinoline derivatives such as metal complex dyes having 8-quinolinol or their derivative as a ligand such as tris(8-quinolinolato)aluminum, tetraphenylbutadiene, anthracene, perylene, coronene, 12-phthaloperynone derivatives, phenylanthracene derivatives, and tetraarylethene derivatives.

It is also possible to use the light emitting layer 5 consisting of a host compound and a dopant (guest compound) in which the above compound is used as the host compound or the dopant.

When the above compound is used as the dopant, the content of the above compound is preferably 0.01 to 20% by weight and more preferably 0.1 to 15% by weight. Using in combination with a host compound, the dopant will change the emitted light wavelength properties of the host compound so as to be able to emit light having a longer wavelength. Furthermore, the light emission efficiency and stability of the device will be improved. On the other hand, when the above compound is used as the host compound, the content of the above compound is preferably 80 to 99.99% by weight and more preferably 85 to 99.99% by weight.

The electron injection/transport layer 6 is capable of facilitating injection of electrons from the negative electrode 7, transporting electrons, and blocking holes. The electron injection/transport layer 6 can be formed by using at least one of the following: quinoline derivatives such as organic metal complexes having 8-quinolinol or their derivative as a ligand such as tris(8-quinolinolato)aluminum, oxadiazole derivatives, triazole derivatives, triazine derivatives, perylene derivatives, quinoline derivatives, quinoxaline derivatives, diphenylquinone derivatives, nitro-substituted fluorenone derivatives, and thiopyrandioxide derivatives. Furthermore, the above compound of the present invention is also a preferable material for the electron injection/transport layer 6. In such a case, the electron transport rate can be controlled, which cannot be adjusted with any prior art electron injection/transport material.

The hole injection/transport layer 4 and electron injection/transport layer 6 are provided as appropriate according to the levels of hole injection, hole transport, electron injection, and electron transport capabilities of the compound used in the light emitting layer 5. For example, if the compound used in the light emitting layer 5 has a high level of hole injection/transport capability or electron injection/transport capability, the light emitting layer 5 can also serve as the hole injection/transport layer 4 or electron injection/transport layer 6 and the hole injection/transport layer 4 or electron injection/transport layer 6 is eliminated. Furthermore, both the hole injection/transport layer 4 and the electron injection/transport layer 6 can be eliminated in some cases.

Furthermore, the hole injection/transport layer 4 and electron injection/transport layer 6 can each be divided into a layer capable of injection and a layer capable of transport. For example, if the electron injection/transport layer 6 is divided into an electron injection layer and an electron transport layer, a preferable combination of compounds selected from the electron transport/injection layer compounds can be used. In such a case, it is preferable to arrange the layers in the descending order of electron affinity from the negative electrode 7; preferably, an electron injection layer in contact with the negative electrode 7 and an electron transport layer in contact with the light emitting layer 5. The same relationship between the electron affinity and layer order applies when two or more electron injection/transport layers are provided.

The negative electrode 7 is preferably made of an electrode material such as a metal, alloy, or electricity-conducting compound having a relatively low work function. Examples of the electrode material of the negative electrode include lithium, lithium-indium alloy, sodium, sodium-potassium alloy, calcium, magnesium, magnesium-silver alloy, magnesium-indium alloy, indium, ruthenium, titanium, manganese, yttrium, aluminum, aluminum-lithium alloy, aluminum-calcium alloy, aluminum-magnesium alloy, and graphite film. These electrode materials can be used alone or in combination. The negative electrode 7 can be formed on the electron injection/transport layer 6 by the above electrode materials through deposition, sputtering, ionized evaporation, ion plating, or cluster ion beam. The negative electrode 7 can have a monolayer or multilayer structure. In order to efficiently retrieve light emitted by the organic EL device, preferably, at least either one of the positive electrode 7 and negative electrodes 3 is transparent or translucent. Generally, the material and thickness of the positive electrode 3 is so determined to transmit 80% or more of the emitted light.

Embodiments of the present invention will be given hereafter along with comparative embodiments to describe the present invention further in detail.

Exemplary Synthesis 1

Synthesis of Compound 1

[Chem 12]

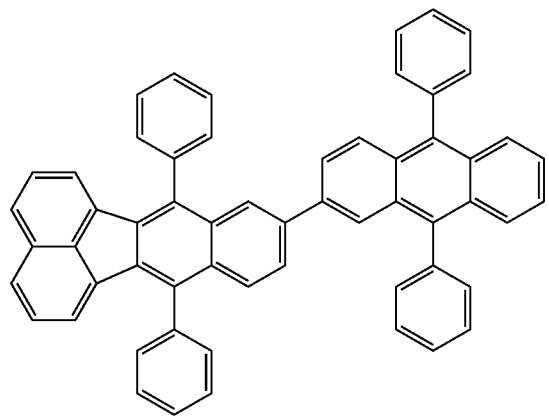

Synthesis of 9,10-diphenylanthracene-2-boronic acid

An amount of 6.8 g (23.7 mmol) of 2-bromoanthraquinone was suspended in a mixed solvent of 50 ml of dehydrated toluene and 50 ml of dehydrated ether and cooled to −20° C. An amount of 26.3 ml (50 mmol) of a solution of phenyl-lithium (1.9 mmol/ml) in butylether was added and allowed to react for six hours. Then, distilled water was added to stop the reaction. Then, the separated organic layer was applied to column chromatography to obtain a diol form. Then, the obtained diol form, 39 g (237 mmol) of potassium iodide, and 41 g (390 mmol) of sodium hypophosphite monohydrate were dissolved in acetic acid and refluxed for six hours. After cooling, the deposit was filtered and purified by column chromatography to obtain 4.68 g (11.4 mmol) of 2-bromo-9,10-diphenylanthracene. The yield was 48.3%.

An amount of 4.68 g (11.4 mmol) of 2-bromo-9,10-diphenylanthracene was dissolved in dehydrated THF and cooled to −80° C. An amount of 7.9 ml (12 mmol) of a solution of n butyllithium in n hexane was added dropwise and, 40 minutes later, 3.33 g (22.8 mmol) of triethyl borate was further added. After two-hour reaction, a dilute hydrochloric acid solution was added and the mixture was allowed to stand for 12 hours. Then, the separated organic layer was recrystallized to obtain 3.07 g (8.2 mmol) of 9,10-diphenylanthracene-2-boronic acid. The yield was 72%.

Synthesis of 9-bromo-7,12-diphenylbenzofluoranthene

An amount of 5.9 g (32.4 mmol) of acenaphthenequinone and 7.5 g (35.7 mmol) of 1,3-diphenyl-2-propanone were suspended in 150 ml of ethanol and a solution of 2 g of potassium hydroxide in ethanol was added. After the mixture was heated to the reflux temperature, the same amount of the solution of potassium hydroxide in ethanol was further added and allowed to react for five minutes. The solid substance deposited after cooled on ice was filtered and washed with ethanol to obtain 8.24 g (23.1 mmol) of 7,9-diphenylcyclopenta[a]acenaphthylene-8-one. The yield was 71.3%.

An amount of 8.24 g (23.1 mmol) of 7,9-diphenylcyclopenta[a]acenaphthylene-8-one was dissolved in 300 ml of dichloromethane and held at the reflux temperature. A solution of 5.4 g (46.2 mmol) of isoamyl nitrite in dichloromethane and a solution of 5 g (23.1 mmol) of 2-amino-5-bromobenzoic acid in dichloromethane were simultaneously added dropwise over one hour. After 12-hour reflux, methanol was added and the deposit was filtered. Then, the deposit was dissolved in xylene, refluxed for 12 hours, and purified by column chromatography to obtain 3.96 g (8.2 mmol) of 9-bromo-7,12-diphenylbenzofluoranthene. The yield was 35.5%.

Synthesis of Compound 1

An amount of 1.4 g (3.74 mmol) of 9,10-diphenylanthracene-2-boronic acid, 1.8 g (3.74 mmol) of 9-bromo-7,12-diphenylbenzofluoranthene, and 100 mg of tetrakis triphenylphosphine palladium as catalysis were dissolved in a mixed solvent of 80 ml of toluene and 20 ml of ethanol. Then, 40 ml of 2M sodium carbonate solution was added and allowed to react at 90° C. for 12 hours. After the reaction was completed, the organic layer was separated and purified by column chromatography to obtain 1.83 g (2.5 mmol) of Compound 1. The yield was 66.8%.

The obtained Compound 1 was identified by the mass spectrum, infrared absorption spectrum, and NMR.

Exemplary Synthesis 2

Synthesis of Compound 2

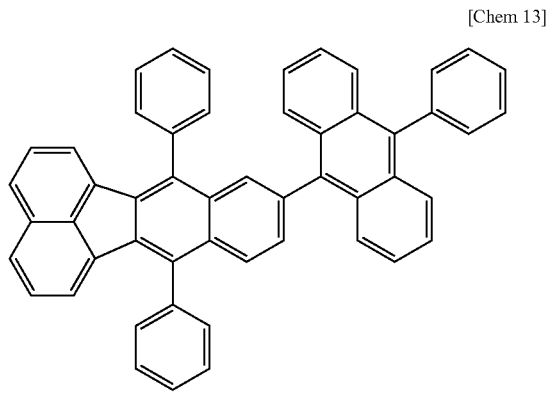 [SMILES: c1ccc(-c2c3c(c(-c4ccccc4)c4cc(-c5c6ccccc6c(-c6ccccc6)c6ccccc56)ccc24)-c2cccc4cccc-3c24)cc1]

[Chem 13]

Synthesis of 10-phenylanthracene-9-boronic acid

An amount of 15.14 g (58.9 mmol) of 9-bromoanthracene, 7.2 g (59 mmol) of phenylboronic acid, and 1 g of tetrakis triphenylphosphine palladium as catalysis were dissolved in a mixed solvent of 100 ml of toluene and 25 ml of ethanol. Then, 50 ml of 2M sodium carbonate solution was added to the mixed solvent and allowed to react at 90° C. for 12 hours. After the reaction was completed, the organic layer was separated and purified by column chromatography to obtain 13.65 g (53.7 mmol) of 9-phenylanthracene. The yield was 91.2%.

An amount of 13.65 g (53.7 mmol) of 9-phenylanthracene was dissolved in 100 ml of N,N dimethylformamide. An amount of 10.5 g (59 mmol) of N bromosuccinimide was added and allowed to react for six hours. Then, distilled water was added to stop the reaction and the deposit was filtered. The recovered deposit was purified by column chromatography to obtain 15.97 g (48 mmol) of 9-bromo-10-phenylanthracene. The yield was 89.3%.

An amount of 14 g (42 mmol) of 9-bromo-10-phenylanthracene was dissolved in dehydrated THF and cooled to −80° C. Then, 31.2 ml (49 mmol) of a solution of n-butyllithium in n-hexane was added dropwise. Forty minutes later, 13 g (89 mmol) of triethyl borate was added. After two-hour reaction, a diluted hydrochloric acid solution was added and allowed to stand for 12 hours. Then, the separated organic layer was recrystallized to obtain 10 g (33.6 mmol) of 10-phenylanthracene-9-boronic acid. The yield was 75.2%.

Synthesis of Compound 2

An amount of 0.94 g (3.14 mmol) of 10-phenylanthracene-9-boronic acid, 1.52 g (3.14 mmol) of 9-bromo-7,12-diphenybenzofluoranthene synthesized in the same manner as in Exemplary Synthesis 1, and 100 mg of tetrakis triphenylphosphine palladium as catalysis were dissolved in a mixed solvent of 80 ml of toluene and 20 ml of ethanol. Then, 40 ml of 2M sodium carbonate solution was added and allowed to react at 90° C. for 12 hours. After the reaction was completed, the organic layer was separated and purified by column chromatography to obtain 1.37 g (2.09 mmol) of Compound 2. The yield was 66.6%.

The obtained Compound 2 was identified by the mass spectrum, infrared absorption spectrum, and NMR.

Exemplary Synthesis 3

Synthesis of Compound 3

[Chem 14]

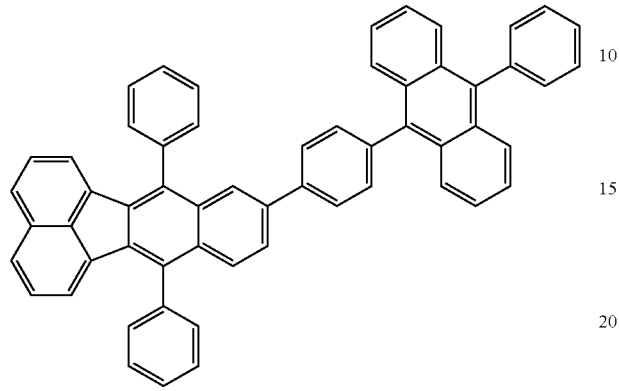

Synthesis of 9-phenyl-10-(4-bromophenyl)anthracene

An amount of 2.46 g (8.26 mmol) of 10-phenylanthracene-9-boronic acid synthesized in the same manner as in Exemplary Synthesis 2, 9.75 g (41.3 mmol) of p-dibromobenzene, and 250 mg of tetrakis triphenylphosphine palladium as catalysis were dissolved in a mixed solvent of 60 ml of toluene and 15 ml of ethanol. Then, 30 ml of 2M sodium carbonate solution was added and allowed to react at 90° C. for 12 hours. After the reaction was completed, the organic layer was separated and purified by column chromatography to obtain 1.48 g (3.62 mmol) of 9-phenyl-10-(4-bromophenyl)anthracene. The yield was 43.8%.

Synthesis of 7,12-diphenylbenzofluoranthene-9-boronic acid

An amount of 3 g (6.21 mmol) of 9-bromo-7,12-diphenylbenzofluoranthene synthesized in the same manner as in Exemplary Synthesis 1 was dissolved in dehydrated THF and cooled to −80° C. Then, 4.3 ml (6.8 mmol) of a solution of n butyllithium in n-hexane was added dropwise. Forty minutes later, 1.81 g (12.4 mmol) of triethyl borate was added. After two-hour reaction, a diluted hydrochloric acid solution was passed and allowed to stand for 12 hours. Then, the separated organic layer was recrystallized to obtain 1.51 g (3.37 mmol) of 7,12-diphenylbenzofluoranthene-9-boronic acid. The yield was 54.3%.

Synthesis of Compound 3

An amount of 1.38 g (3.37 mmol) of 9-phenyl-10-(4-bromophenyl)anthracene, 1.51 g (3.37 mmol) of 7,12-diphenylbenzofluoranthene-9-boronic acid, and 100 mg of tetrakis triphenylphosphine palladium as catalysis were dissolved in a mixed solvent of 60 ml of toluene and 15 ml of ethanol. Then, 30 ml of 2M sodium carbonate solution was added and allowed to react at 90° C. for 12 hours. After the reaction was completed, the organic layer was separated and purified by column chromatography to obtain 2.01 g (2.75 mmol) of Compound 3. The yield was 81.6%.

The obtained Compound 3 was identified by the mass spectrum, infrared absorption spectrum, and NMR.

Exemplary Synthesis 4

Synthesis of Compound 4

[Chem 15]

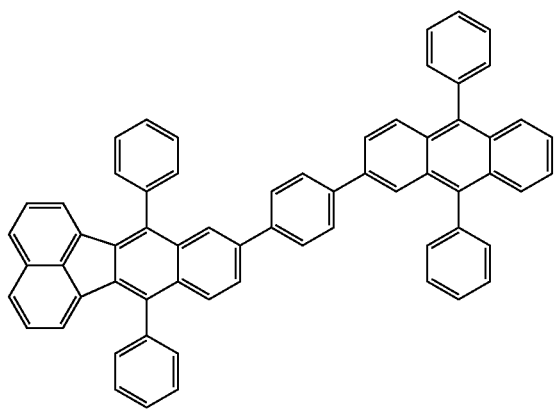

Synthesis of 2-(4-bromophenyl)-9,10-diphenylanthracene

An amount of 3.74 g (10 mmol) of 9,10-diphenylanthracene-2-boronic acid synthesized in the same manner as in Exemplary Synthesis 1, 9.44 g (40 mmol) of p-dibromobenzene, and 300 mg of tetrakis triphenylphosphine palladium as catalysis were dissolved in a mixed solvent of 60 ml of toluene and 15 ml of ethanol. Then, 30 ml of 2M sodium carbonate solution was added and allowed to react at 90° C. for 12 hours. After the reaction was completed, the organic layer was separated and purified by column chromatography to obtain 2.32 g (5.15 mmol) of 2-(4-bromophenyl)-9,10-diphenylanthracene. The yield was 51.5%.

Synthesis of Compound 4

An amount of 1.35 g (3 mmol) of 2-(4-bromophenyl)-9,10-diphenylanthracene, 1.34 g (3 mmol) of 7,12-diphenylbenzofluoranthene-9-boronic acid synthesized in the same manner as in Exemplary Synthesis 3, and 100 mg of tetrakis triphenylphosphine palladium as catalysis were dissolved in a mixed solvent of 60 ml of toluene and 15 ml of ethanol. Then, 30 ml of 2M sodium carbonate solution was added and allowed to react at 90° C. for 12 hours. After the reaction was completed, the organic layer was separated and purified by column chromatography to obtain 1.68 g (2.08 mmol) of Compound 4. The yield was 69.3%.

The obtained Compound 4 was identified by the mass spectrum, infrared absorption spectrum, and NMR.

Exemplary Synthesis 5

Synthesis of Compound 5

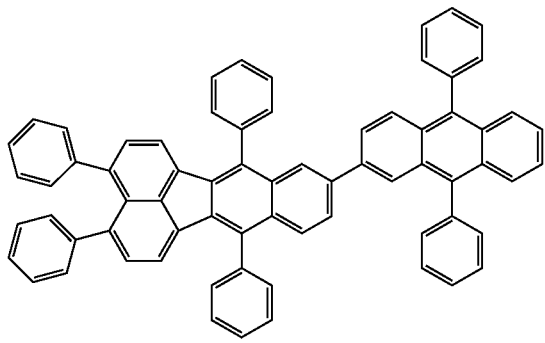

[Chem 16]

Synthesis of 9-bromo-3,4,7,12-tetraphenylbenzofluoranthene

An amount of 6.8 g (20 mmol) of 3,4-dibromoacenaphthenequinone, 6.1 g (50 mmol) of phenylboronic acid, and 1 g of tetrakis triphenylphosphine palladium as catalysis were dissolved in a mixed solvent of 80 ml of toluene and 20 ml of ethanol. Then, 40 ml of 2M sodium carbonate solution was added and allowed to react at 90° C. for 12 hours. After the reaction was completed, the organic layer was separated and purified by column chromatography to obtain 3.85 g (11.5 mmol) of 3,4-diphenylacenaphthenequinone. The yield was 57.5%.

An amount of 3.85 g (11.5 mmol) of 3,4-diphenylacenaphthenequinone and 2.7 g (12.9 mmol) of 1,3-diphenyl-2-propanone were suspended in 50 ml of ethanol and a solution of 0.4 g of potassium hydroxide in ethanol was added. After the mixture was heated to the reflux temperature, the same amount of the solution of potassium hydroxide in ethanol was further added and allowed to react for five minutes. The solid substance deposited after cooled on ice was filtered and washed with ethanol to obtain 2.82 g (5.55 mmol) of 3,4,7,9-tetraphenylcyclopenta[a]acenaphthylene-8-one. The yield was 48.3%.

An amount of 2.82 g (5.55 mmol) of 3,4,7,9-tetraphenylcyclopenta[a]acenaphthylene-8-one was dissolved in 100 ml of dichloromethane and held at the reflux temperature. A solution of 1.3 g (11.1 mmol) of isoamyl nitrite in dichloromethane and a solution of 1.2 g (5.55 mmol) of 2-amino-5-bromobenzoic acid in dichloromethane were simultaneously added dropwise over one hour. After 12-hour reflux, methanol was added and the deposit was filtered. Then, the deposit was dissolved in xylene, refluxed for 12 hours, and purified by column chromatography to obtain 0.76 g (1.2 mmol) of 9-bromo-3,4,7,12-tetraphenylbenzofluoranthene. The yield was 21.6%.

Synthesis of Compound 5

An amount of 0.76 g (1.2 mmol) of 9-bromo-3,4,7,12-tetraphenylbenzofluoranthene, 0.45 g (1.2 mmol) of 9,10-diphenylanthracene-2-boronic acid synthesized in the same manner as in Exemplary Synthesis 1, and 15 mg of tetrakis triphenylphosphine palladium as catalysis were dissolved in a mixed solvent of 40 ml of toluene and 10 ml of ethanol. Then, 20 ml of 2M sodium carbonate solution was added and allowed to react at 90° C. for 12 hours. After the reaction was completed, the organic layer was separated and purified by column chromatography to obtain 0.78 g (0.88 mmol) of Compound 5. The yield was 73.3%.

Exemplary Synthesis 6

Synthesis of Compound 6

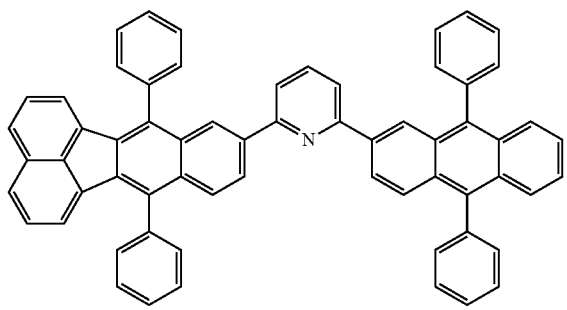

[Chem 17]

Compound 6 was obtained in the same manner as in Exemplary Synthesis 4 except that p-dibromobenzene was replaced by 2,6-dibromopyridine.

Exemplary Synthesis 7

Synthesis of Compound 7

[Chem 18]

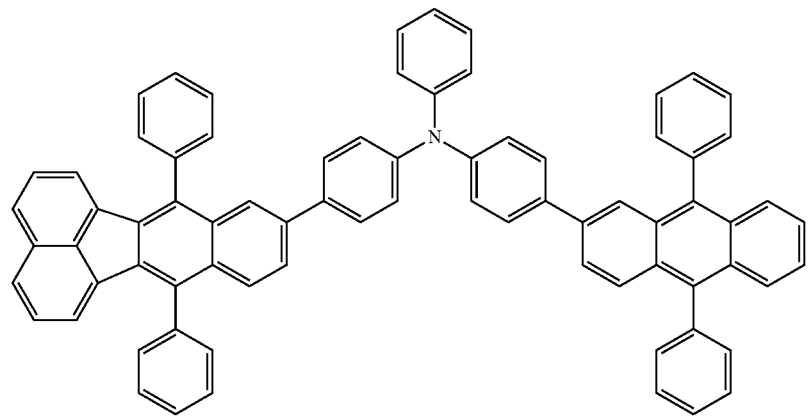

Compound 7 was obtained in the same manner as in Exemplary Synthesis 4 except that p-dibromobenzene was replaced by 4,4'-dibromotriphenylamine.

Exemplary Synthesis 8

Synthesis of Compound 8

[Chem 19]

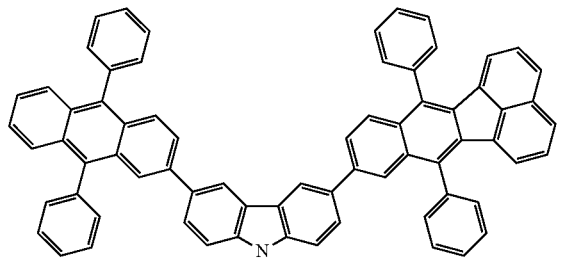

Compound 8 was obtained in the same manner as in Exemplary Synthesis 4 except that p-dibromobenzene was replaced by 3,6'-dibromocarbazole.

Exemplary Synthesis 9

Synthesis of Compound 9

[Chem 20]

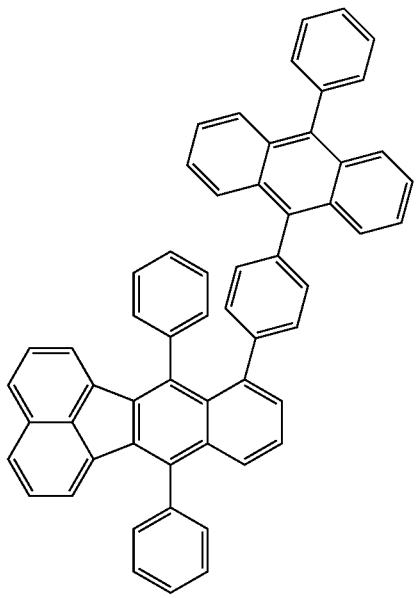

Synthesis of
8-bromo-7,12-diphenylbenzofluoranthene 8-bromo-7,12-diphenylbenzofluoranthene was obtained in the same manner as in Exemplary Synthesis 1 except that 2-amino-5-bromobenzoic acid was replaced by 2-amino-3-bromobenzoic acid.

Synthesis of Compound 9

Compound 9 was obtained in the same manner as in Exemplary Synthesis 3 except that 9-bromo-7,12-diphenylbenzofluoranthene was replaced by 8-bromo-7,12-diphenylbenzofluoranthene.

Exemplary Synthesis 10

Synthesis of Compound 10

[Chem 21]

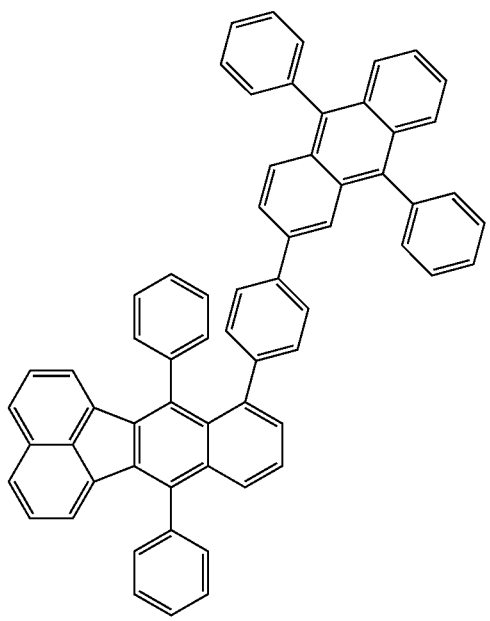

Synthesis of
8-bromo-7,12-diphenylbenzofluoranthene 8-bromo-7,12-diphenylbenzofluoranthene was obtained in the same manner as in Exemplary Synthesis 1 except that 2-amino-5-bromobenzoic acid was replaced by 2-amino-3-bromobenzoic acid.

Synthesis of Compound 10

Compound 10 was obtained in the same manner as in Exemplary Synthesis 4 except that 9-bromo-7,12-diphenylbenzofluoranthene was replaced by 8-bromo-7,12-diphenylbenzofluoranthene.

Embodiment 1

A transparent ITO electrode film was formed on a glass substrate to a thickness of 100 nm by RF sputtering and patterned. The glass substrate with the transparent ITO electrode was subjected to ultrasonic cleaning with a neutral detergent, acetone, and ethanol, pulled out of boiling ethanol, and dried. The transparent electrode surface was subjected to UV/$O_3$ cleaning and then fixed to a substrate holder in a vacuum deposition unit, which was vacuumed to $1\times10^{-4}$ Pa or lower.

With the vacuumed state maintained, N,N'-diphenyl-N,N'-bis[N-(4-methylphenyl)-N-phenyl-(4-aminophenyl)]-1,1'-biphenyl-4,4'-diamine having the structure below was deposited to a thickness of 50 nm at a deposition rate of 0.1 nm/sec to form a hole injection layer.

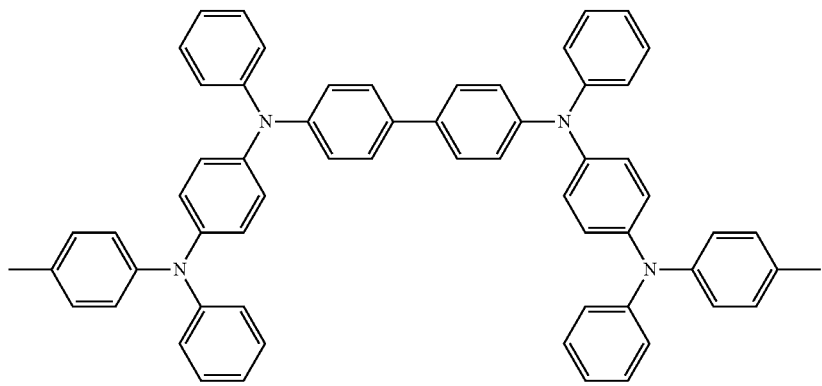

Then, N,N,N',N'-tetrakis(m-biphenyl)-1,1'-biphenyl-4,4'-diamine having the structure below was deposited to a thickness of 10 nm at a deposition rate of 0.1 nm/sec to form a hole transport layer.

[Chem 23]

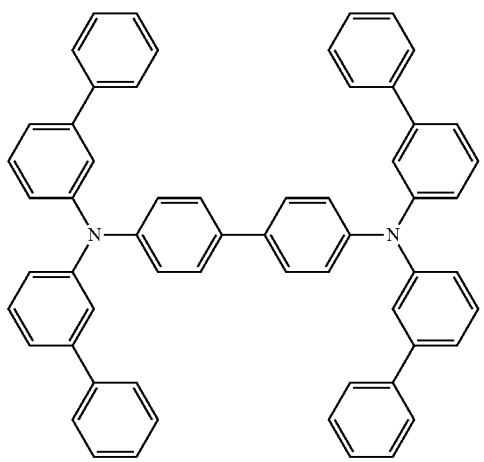

Furthermore, with the vacuum state maintained, the compound of Exemplary Synthesis 1 as a host material and a compound having the structure below as a dopant were deposited to a thickness of 40 nm with a mass ratio of 98:2 at an overall deposition rate of 0.1 nm/sec to form a light emitting layer.

[Chem 24]

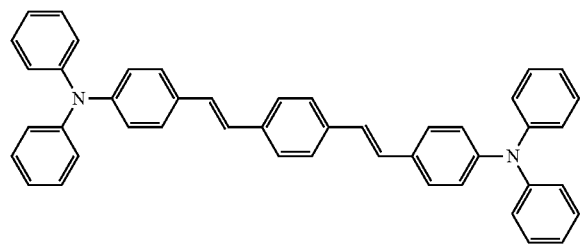

Then, with the vacuum state maintained, the Compound 1 of Exemplary Synthesis 1 and then tris(8-hydroxyquinoline) aluminum (Alq3) were deposited to a thickness of 10 nm and nm, respectively, at a deposition rate of 0.1 nm/sec to form an electron injection/transport layer.

Then, LiF was deposited to a thickness of 0.5 nm at a deposition rate of 0.1 nm/sec to form an electron injection electrode and Al was deposited to a thickness of 100 nm to form a protective electrode. Finally, glass sealing was applied to obtain an organic EL device.

A DC voltage was applied to the organic EL device. With an initial current density of mA/cm$^2$, a drive voltage of 6.7 V and cyan light emission of 1312 cd/m$^2$ were observed. The observed chromaticity was (x, y)=(0.155, 0.359).

[Chem 22]

Embodiment 2

An organic EL device was obtained in the same manner as in Embodiment 1 except that the host material of the light emitting layer was replaced by the Compound 2 of Exemplary Synthesis 2.

A DC voltage was applied to the obtained organic EL device. With an initial current density of 10 mA/cm$^2$, a drive voltage of 6.5 V and cyan light emission of 1387 cd/m$^2$ were observed. The observed chromaticity was (x, y)=(0.152, 0.345).

Embodiment 3

An organic EL device was obtained in the same manner as in Embodiment 1 except that the host material of the light emitting layer was replaced by the Compound 3 of Exemplary Synthesis 3.

A DC voltage was applied to the obtained organic EL device. With an initial current density of 10 mA/cm$^2$, a drive voltage of 6.3 V and cyan light emission of 1455 cd/m$^2$ were observed. The observed chromaticity was (x, y)=(0.150, 0.337).

Embodiment 4

Organic EL devices were obtained in the same manner as in Embodiment 1 except that the host material of the light emitting layer was replaced by the Compounds 4 to 10 of Exemplary Synthesis 4 to 10. A DC voltage was applied to the obtained organic EL devices. With an initial current density of 10 mA/cm$^2$, cyan light emission nearly equal to that of Embodiment 3 was observed. As for the chromaticity, nearly the same results were observed.

Embodiment 5

Comparative Embodiments 1 to 3

A transparent ITO electrode film was formed on a glass substrate to a thickness of 100 nm by RF sputtering and patterned. The glass substrate with the transparent ITO electrode was subjected to ultrasonic cleaning with a neutral detergent, acetone, and ethanol, pulled out of boiling ethanol, and dried. The transparent electrode surface was subjected to $UV/O_3$ cleaning and then fixed to a substrate holder in a vacuum deposition unit, which was vacuumed to $1\times10^{-4}$ Pa or lower.

With the vacuumed state maintained, N,N'-diphenyl-N,N'-bis[N-(4-methylphenyl)-N-phenyl-(4-aminophenyl)]-1,1'-biphenyl-4,4'-diamine having the structure below was deposited to a thickness of 30 nm at a deposition rate of 0.1 nm/sec to form a hole injection layer.

[Chem 25]

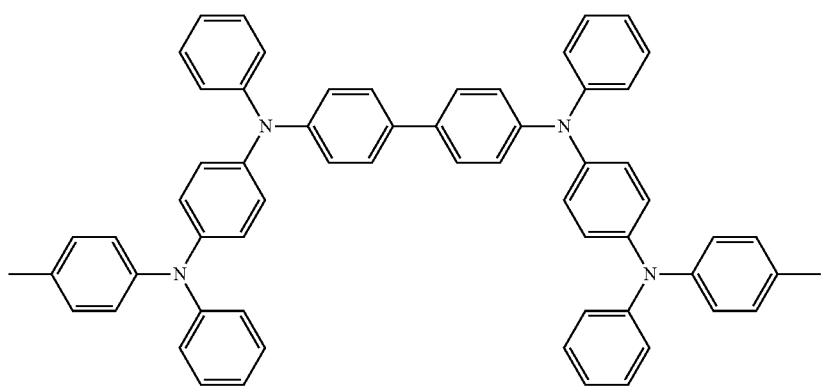

Then, N,N,N',N'-tetrakis(m-biphenyl)-1,1'-biphenyl-4,4'-diamine having the structure below was deposited to a thickness of 65 nm at a deposition rate of 0.1 nm/sec to form a hole transport layer.

[Chem 26]

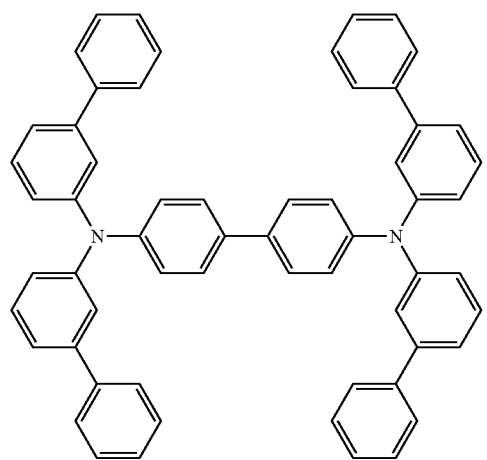

Furthermore, with the vacuum state maintained, a naphthacene derivative having the structure below as a host material and an indenoperylene derivative having the structure below as a dopant were deposited to a thickness of 40 nm with a mass ratio of 99.5:0.5 at an overall deposition rate of 0.1 nm/sec to form a light emitting layer.

[Chem 27]

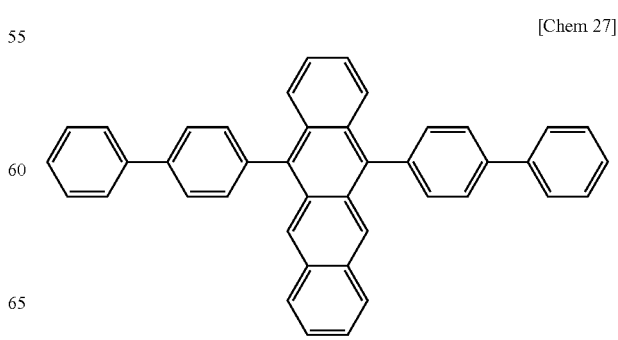

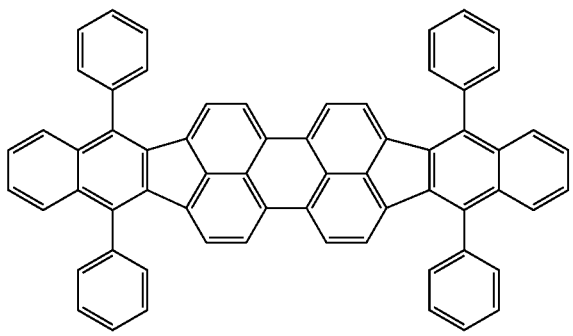

Then, with the vacuum state maintained, a hole-blocking layer was deposited to a thickness of 20 nm at a deposition rate of 0.1 nm/sec. The following four compounds were used as the material of the hole-blocking layer to obtain devices (HBL1 (Embodiment 5) and HBL2 to HBL4 (Comparative Embodiments 1 to 3)) for comparison.

[Chem 28]

HBL1

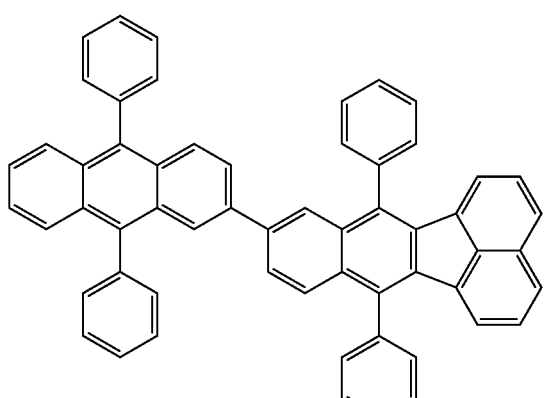

HBL2

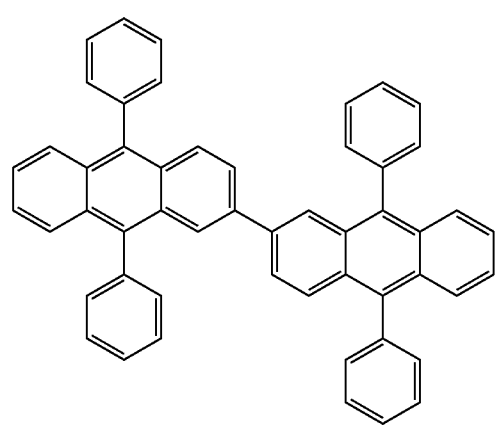

HBL3

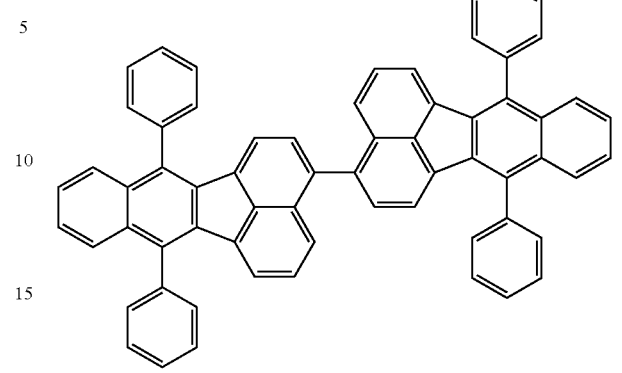

HBL4

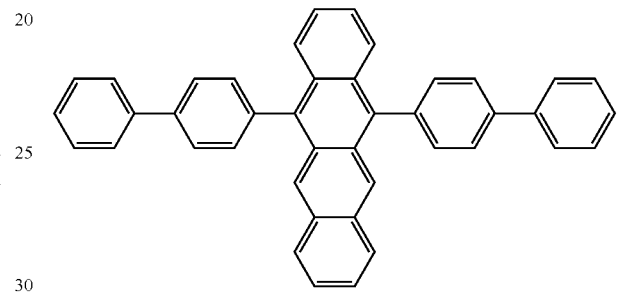

Then, with the vacuum state maintained, a naphthacene derivative having the structure below and then tris(8-hydroxy quinoline)aluminum (Alq 3) were deposited to a thickness of 30 nm and 4 nm, respectively, at a deposition rate of 0.1 nm/sec to form an electron injection/transport layer.

[Chem 29]

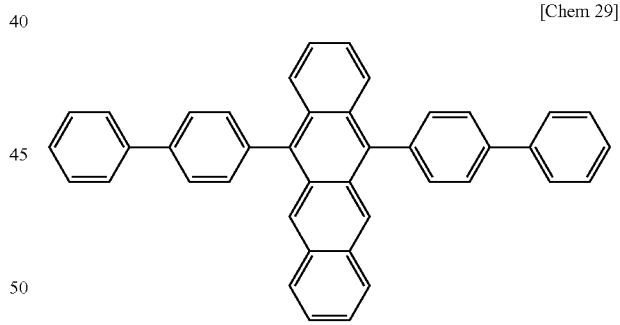

Then, LiF was deposited to a thickness of 0.5 nm at a deposition rate of 0.1 nm/sec to form an electron injection electrode and Al was deposited to a thickness of 100 nm to form a protective electrode. Finally, glass sealing was applied to obtain organic EL devices.

A DC voltage was applied to the four levels of organic EL devices with a current density of 1000 mA/cm² for comparison. Generally, under a high electric field such as 1000 mA/cm², the carrier recoupling rate drops and, consequently, the light emission efficiency drops. The effectiveness of the carrier-blocking layer is important for preventing the drop in efficiency under such a circumstance. Table 1 shows the light emission efficiency of the four levels of organic EL devices driven with 1000 mA/cm².

TABLE 1

| | current efficiency | voltage |
|---|---|---|
| Embodiment 5 (HLB1) | 6.5 cd/A | 6.99 V |
| Comparative Embodiment 1 (HLB2) | 5.9 cd/A | 7.09 V |
| Comparative Embodiment 2 (HLB3) | 6.2 cd/A | 8.35 V |
| Comparative Embodiment 3 (HLB4) | 5.6 cd/A | 6.51 V |

As shown in Table 1, HBL1 of Embodiment 5 having physical properties between anthracene and fluoranthene exhibits balanced and higher quality properties both in current efficiency and in voltage.

Comparative Embodiment 4

An organic EL device was obtained in the same manner as in Embodiment 1 except that the host material of the light emitting layer was replaced by a compound having the structure below.

[Chem 30]

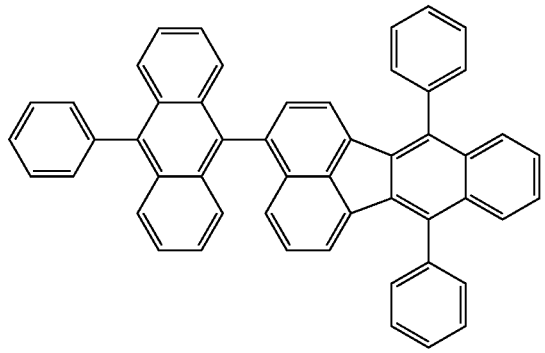

A DC voltage was applied to the obtained organic EL device. With a current density of 10 mA/cm², a drive voltage of 7.7 V and whitish cyan light emission of 1215 cd/m² were observed. The observed chromaticity was (x, y)=(0.205, 0.367) and the target chromaticity was not achieved. This was presumably because a trace amount of contaminants having long wavelength components were produced in the host material during sublimation purification or during heating in deposition. As for the contaminants, the compound obtained after sublimation purification was separated by HPLC and the UV-visible absorption spectrum was measured. The spectrum was identical to the UV-visible absorption spectrum of the structure below.

[Chem 31]

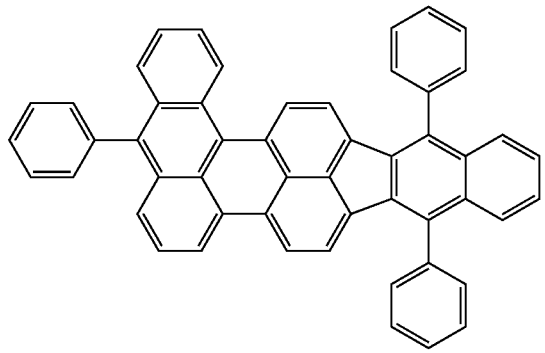

Having described and illustrated the principles of this application by reference to one (or more) preferred embodiment(s), it should be apparent that the preferred embodiments may be modified in arrangement and detail without departing from the principles disclosed herein and that it is intended that the application be construed as including all such modifications and variations insofar as they come within the spirit and scope of the subject matter disclosed herein.

What is claimed is:

1. An organic EL device having at least one organic compound layer containing a compound indicated by any one of the below compounds Chem 1-10:

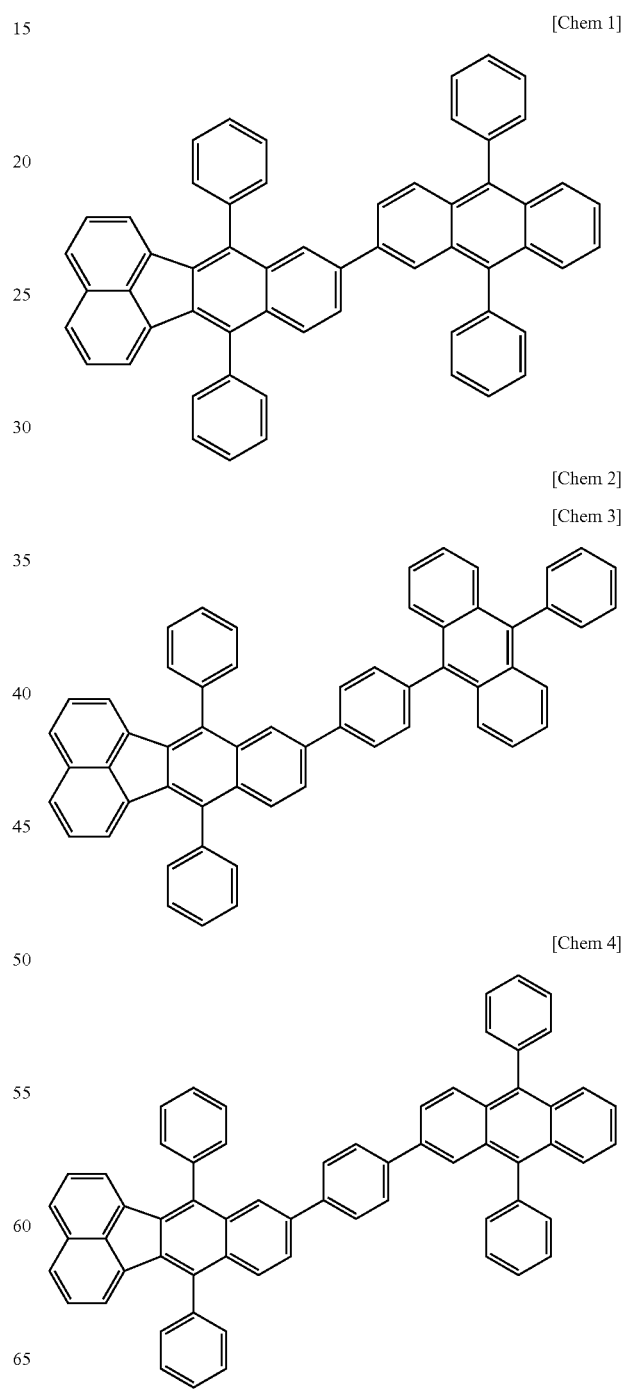

[Chem 5]
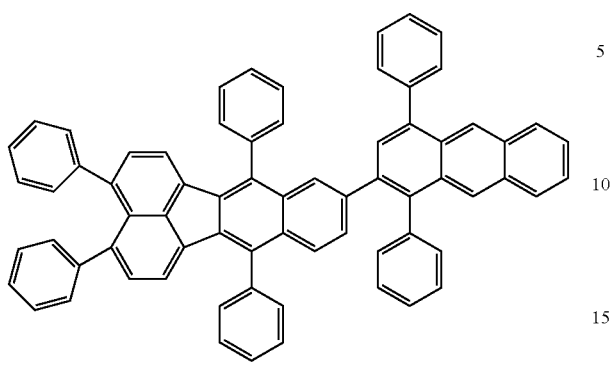
[Chem 6]
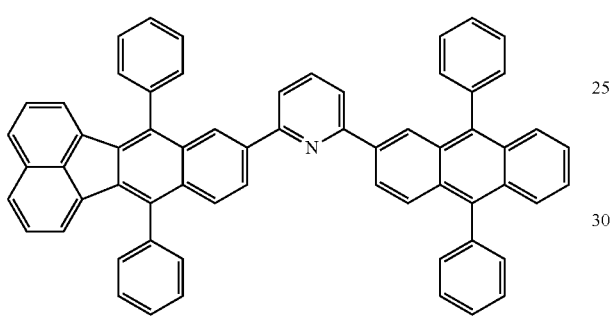
[Chem 7]
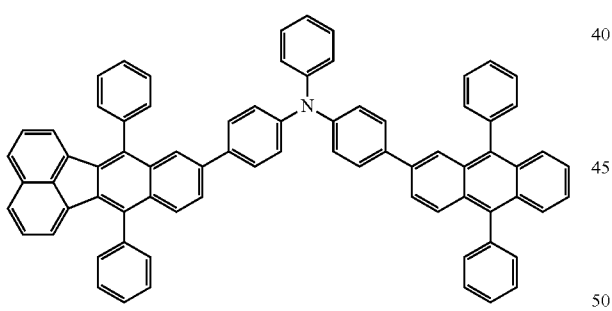
[Chem 8]
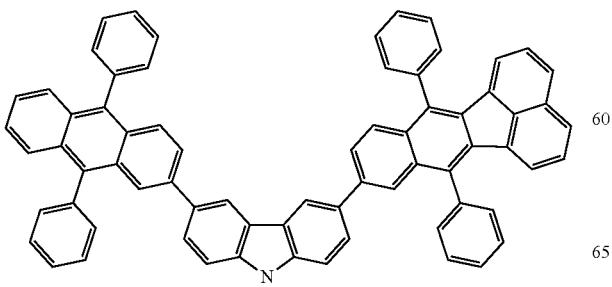
[Chem 9]
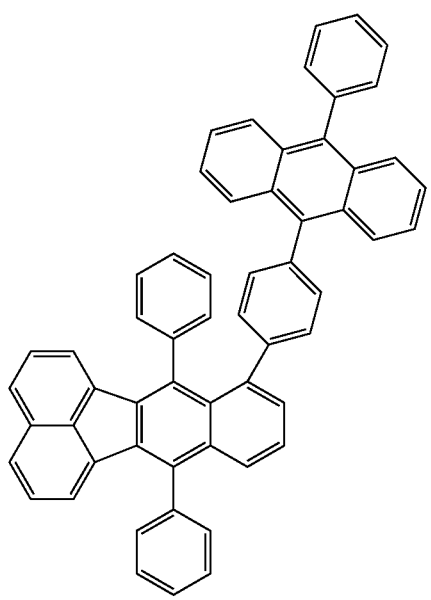
[Chem 10]
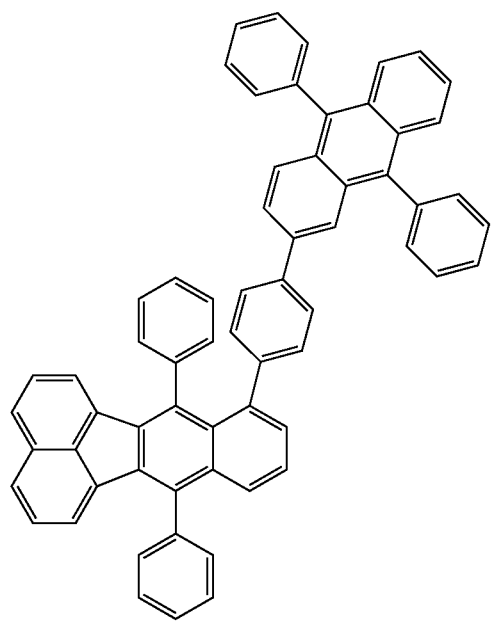
2. An organic EL device having at least one organic compound layer containing a compound indicated by one of the below compounds Chem 11 and 12:

[Chem 11]

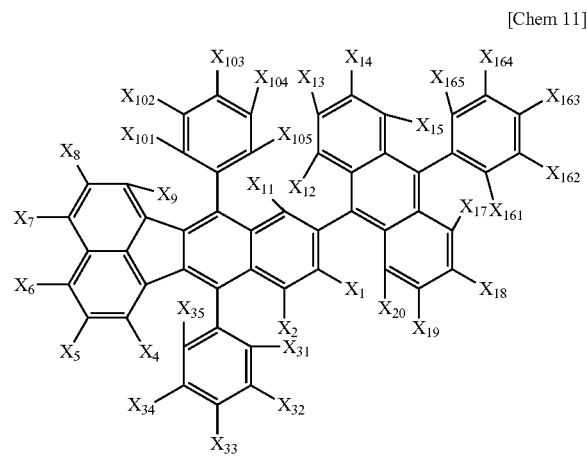

[Chem 12]

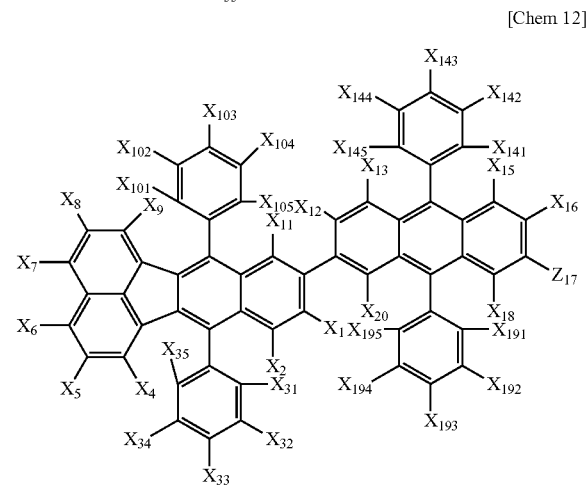

in which $X_1$-$X_{20}$ indicates a hydrogen atom, phenyl group, naphthyl group, anthryl group, phenanthryl group, pyrenyl group, perylenyl group, (o-, m-, or p-) biphenylyl group (in which the phenyl group, naphthyl group, anthryl group, phenanthryl group, pyrenyl group, perylenyl group, or (o-, m-, or p-) biphenylyl group is optionally further substituted by an alkyl group, alkoxy group, aryl group, aryloxy group, amino group, or halogen atom), methyl group, ethyl group, (n- or i-) propyl group, (n-, i-, s-, or t-) butyl group, diphenylamino group, ditolylamino group, dibiphenylylamino group, N-phenyl-N-tolylamino group, N-phenyl-N-naphthylamino group, N-phenyl-N-biphenylylamino group, N-phenyl-N-anthrylamino group, N-phenyl-N-pyrenylamino group, dinaphthylamino group, diathrylamino group, or dipyrenylamino group; and $X_{31}$-$X_{195}$ indicates a hydrogen atom, alkyl group, alkoxy group, aryl group, aryloxy group, amino group, or halogen atom.

3. The organic EL device according to claim 2, wherein said X1-X20 group is a hydrogen atom or phenyl group, and said X31-X195 group is a hydrogen atom, alkyl group, alkoxy group, aryl group, aryloxy group, amino group, or halogen atom.

4. The organic EL device according to claim 2, wherein said $X_1$-$X_{20}$ group is a hydrogen atom or phenyl group, and said $X_{31}$-$X_{195}$ group is a hydrogen atom or methyl group.

5. The organic EL device according to claim 2, wherein said $X_1$, $X_2$, $X_4$, $X_5$, $X_8$, $X_9$, $X_{11}$, $X_{12}$, $X_{14}$, $X_{15}$, $X_{17}$, $X_{19}$ and $X_{20}$ indicates a hydrogen atom, said $X_6$, $X_7$, $X_{13}$, $X_{16}$, and $X_{18}$ indicates a hydrogen atom, phenyl group, naphthyl group, anthryl group, phenanthryl group, pyrenyl group, perylenyl group, (o-, m-, or p-) biphenylyl group (in which the phenyl group, naphthyl group, anthryl group, phenanthryl group, pyrenyl group, perylenyl group, or (o-, m-, or p-) biphenylyl group is optionally further substituted by an alkyl group, alkoxy group, aryl group, aryloxy group, amino group, or halogen atom), methyl group, ethyl group, (n- or i-) propyl group, (n-, i-, s-, or t-) butyl group, diphenylamino group, ditolylamino group, dibiphenylylamino group, N-phenyl-N-tolylamino group, N-phenyl-N-naphthylamino group, N-phenyl-N-biphenylylamino group, N-phenyl-N-anthrylamino group, N-phenyl-N-pyrenylamino group, dinaphthylamino group, diathrylamino group, or dipyrenylamino group, and said $X_{31}$-$X_{195}$ indicates a hydrogen atom, alkyl group, alkoxy group, aryl group, aryloxy group, amino group, or halogen atom.

6. The organic EL device according to claim 5, wherein said $X_6$, $X_7$, $X_{13}$, $X_{16}$, and $X_{18}$ indicates a hydrogen atom or phenyl group, and said $X_{31}$-$X_{195}$ indicates a hydrogen atom or methyl group.

* * * * *